(12) United States Patent
Tamarkin et al.

(10) Patent No.: US 8,518,376 B2
(45) Date of Patent: *Aug. 27, 2013

(54) OIL-BASED FOAMABLE CARRIERS AND FORMULATIONS

(75) Inventors: Dov Tamarkin, Ness Ziona (IL); David Schuz, Moshav Gimzu (IL); Yohan Hazot, Givat Shmuel (IL); Elana Gazal, Rehovot (IL)

(73) Assignee: Foamix Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/123,213

(22) PCT Filed: Oct. 6, 2009

(86) PCT No.: PCT/IB2009/007184
§ 371 (c)(1),
(2), (4) Date: Jul. 18, 2011

(87) PCT Pub. No.: WO2010/041141
PCT Pub. Date: Apr. 15, 2010

(65) Prior Publication Data
US 2011/0268665 A1    Nov. 3, 2011

Related U.S. Application Data

(63) Continuation-in-part of application No. 12/795,164, filed on Jun. 7, 2010, which is a continuation of application No. PCT/IB2008/003932, filed on Dec. 8, 2008, and a continuation-in-part of application No. 12/795,213, filed on Jun. 7, 2010, which is a continuation of application No. PCT/IB2008/003939, filed on Dec. 8, 2008.

(60) Provisional application No. 61/103,500, filed on Oct. 7, 2008, provisional application No. 61/120,842, filed on Dec. 8, 2008, provisional application No. 61/012,414, filed on Dec. 7, 2007.

(51) Int. Cl.
*A01N 25/16* (2006.01)
*A01P 1/00* (2006.01)
*A61K 31/00* (2006.01)
*A61P 31/00* (2006.01)
*A61Q 19/00* (2006.01)

(52) U.S. Cl.
USPC .......................................................... 424/43

(58) Field of Classification Search
None
See application file for complete search history.

(56) References Cited

U.S. PATENT DOCUMENTS

| | | | |
|---|---|---|---|
| 1,159,250 A | 11/1915 | Moulton | |
| 1,666,684 A | 4/1928 | Carstens | |
| 1,924,972 A | 8/1933 | Beckert | |
| 2,085,733 A | 7/1937 | Bird | |
| 2,390,921 A | 12/1945 | Clark | |
| 2,524,590 A | 10/1950 | Boe | |
| 2,586,287 A | 2/1952 | Apperson | |
| 2,617,754 A | 11/1952 | Neely | |
| 2,767,712 A | 10/1956 | Waterman | |
| 2,968,628 A | 1/1961 | Reed | |
| 3,004,894 A | 10/1961 | Johnson et al. | |
| 3,062,715 A | 11/1962 | Reese et al. | |
| 3,067,784 A | 12/1962 | Gorman | |
| 3,092,255 A | 6/1963 | Hohman | |
| 3,092,555 A | 6/1963 | Horn | |
| 3,141,821 A | 7/1964 | Compeau | |
| 3,142,420 A | 7/1964 | Gawthrop | |
| 3,144,386 A | 8/1964 | Brightenback | |
| 3,149,543 A | 9/1964 | Naab | |
| 3,154,075 A | 10/1964 | Weckesser | |
| 3,178,352 A | 4/1965 | Erickson | |
| 3,236,457 A | 2/1966 | Kennedy et al. | |
| 3,244,589 A | 4/1966 | Sunnen | |
| 3,252,859 A | 5/1966 | Silver | |
| 3,261,695 A | 7/1966 | Sienkiewicz | |
| 3,263,867 A | 8/1966 | Lehmann | |
| 3,263,869 A | 8/1966 | Corsette | |
| 3,298,919 A | 1/1967 | Bishop et al. | |
| 3,301,444 A | 1/1967 | Wittke | |
| 3,303,970 A | 2/1967 | Breslau et al. | |
| 3,330,730 A | 7/1967 | Hernandez | |
| 3,333,333 A | 8/1967 | Noack | |
| 3,346,451 A | 10/1967 | Collins et al. | |
| 3,366,494 A | 1/1968 | Bower et al. | |
| 3,369,034 A | 2/1968 | Chalmers | |

(Continued)

FOREIGN PATENT DOCUMENTS

| AU | 198780257 | 9/1986 |
|---|---|---|
| CA | 2422244 | 9/2003 |

(Continued)

OTHER PUBLICATIONS

Shrestha et al., Foaming Properties of Monoglycerol Fatty Acid Esters in Nonpolar Oil Systems, 2006, Langmuir, vol. 22, pp. 8337-8345.*
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.

(Continued)

*Primary Examiner* — Brian-Yong Kwon
*Assistant Examiner* — Mark V Stevens
(74) *Attorney, Agent, or Firm* — Fish & Richardson P.C.

(57) ABSTRACT

A waterless foamable carrier and pharmaceutical composition which is suitable for external and internal administration is disclosed. The composition is single phase and includes at least one liquid oil; and a glyceride. Pharmaceutical compositions comprising active agents, methods for their preparation, propellants suitable for use with the carriers and uses thereof are further described.

34 Claims, 2 Drawing Sheets

(56) References Cited

U.S. PATENT DOCUMENTS

| | | |
|---|---|---|
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |

| Patent | Date | Inventor |
|---|---|---|
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |

| | | |
|---|---|---|
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,358,541 B1 | 3/2002 | Goodman |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,455,076 B1 | 9/2002 | Hahn et al. |
| 6,468,989 B1 | 10/2002 | Chang et al. |
| 6,479,058 B1 | 11/2002 | McCadden |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B2 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,902,737 B2 | 6/2005 | Quemin et al. |
| 6,911,211 B2 | 6/2005 | Eini et al. |
| 6,946,120 B2 | 9/2005 | Wai-Chiu So et al. |

| | | | | | |
|---|---|---|---|---|---|
| 6,946,139 B2 | 9/2005 | Henning | 2003/0195128 A1 | 10/2003 | Deckman et al. |
| 6,951,654 B2 | 10/2005 | Malcolm et al. | 2003/0206955 A1 | 11/2003 | Sonneville-Aubrun et al. |
| 6,955,816 B2 | 10/2005 | Klysz | 2003/0215472 A1 | 11/2003 | Bonda et al. |
| 6,956,062 B2 | 10/2005 | Beilfuss et al. | 2004/0018228 A1 | 1/2004 | Fischell et al. |
| 6,958,154 B2 | 10/2005 | Andolino Brandt et al. | 2004/0028752 A1 | 2/2004 | Kamm et al. |
| 6,967,023 B1 | 11/2005 | Eini et al. | 2004/0038912 A1 | 2/2004 | Michelet et al. |
| 6,968,982 B1 | 11/2005 | Burns | 2004/0053797 A1 | 3/2004 | Chen et al. |
| 6,969,521 B1 | 11/2005 | Gonzalez et al. | 2004/0058878 A1 | 3/2004 | Walker |
| RE38,964 E | 1/2006 | Shillington | 2004/0063787 A1 | 4/2004 | Villanueva |
| 6,994,863 B2 | 2/2006 | Eini et al. | 2004/0067970 A1 | 4/2004 | Foster et al. |
| 7,002,486 B2 | 2/2006 | Lawrence | 2004/0072638 A1 | 4/2004 | Enos et al. |
| 7,014,844 B2 | 3/2006 | Mahalingam et al. | 2004/0076651 A1 | 4/2004 | Brocks et al. |
| 7,021,499 B2 | 4/2006 | Hansen et al. | 2004/0078896 A1 | 4/2004 | Hellyer et al. |
| 7,029,659 B2 | 4/2006 | Abram | 2004/0079361 A1 | 4/2004 | Clayton et al. |
| 7,060,253 B1 | 6/2006 | Mundschenk | 2004/0105825 A1 | 6/2004 | Henning |
| 7,078,058 B2 | 7/2006 | Jones et al. | 2004/0120917 A1 | 6/2004 | Perrier et al. |
| 7,083,799 B1 | 8/2006 | Giacomoni | 2004/0127554 A1 | 7/2004 | Ghisalberti |
| 7,137,536 B2 | 11/2006 | Walters et al. | 2004/0138179 A1 | 7/2004 | Goldstein et al. |
| 7,195,135 B1 | 3/2007 | Garcia | 2004/0151671 A1 | 8/2004 | Abram et al. |
| 7,222,802 B2 | 5/2007 | Sweeton | 2004/0151756 A1 | 8/2004 | Richards et al. |
| 7,225,518 B2 | 6/2007 | Eidenschink et al. | 2004/0161447 A1 | 8/2004 | Paul |
| 7,226,230 B2 | 6/2007 | Liberatore | 2004/0184992 A1 | 9/2004 | Abram |
| 7,235,251 B2 | 6/2007 | Hamer et al. | 2004/0185123 A1 | 9/2004 | Mazzio et al. |
| 7,270,828 B2 | 9/2007 | Masuda et al. | 2004/0191196 A1 | 9/2004 | Tamarkin |
| 7,455,195 B2 | 11/2008 | Mekata | 2004/0192754 A1 | 9/2004 | Shapira et al. |
| 7,497,354 B2 | 3/2009 | Decottignies et al. | 2004/0195276 A1 | 10/2004 | Fuchs |
| 7,575,739 B2 | 8/2009 | Tamarkin et al. | 2004/0197276 A1 | 10/2004 | Takase et al. |
| 7,645,803 B2 | 1/2010 | Tamarkin et al. | 2004/0197295 A1 | 10/2004 | Riedel et al. |
| 7,654,415 B2 | 2/2010 | van der Heijden | 2004/0219122 A1 | 11/2004 | Masuda et al. |
| 7,682,623 B2 | 3/2010 | Eini et al. | 2004/0219176 A1 | 11/2004 | Dominguez |
| 7,700,076 B2 | 4/2010 | Tamarkin et al. | 2004/0220187 A1 | 11/2004 | Stephenson et al. |
| 7,704,518 B2 | 4/2010 | Tamarkin et al. | 2004/0229813 A1 | 11/2004 | DiPiano et al. |
| 7,793,807 B2 | 9/2010 | Goujon et al. | 2004/0234475 A1 | 11/2004 | Lannibois-Drean et al. |
| 7,820,145 B2 | 10/2010 | Tamarkin et al. | 2004/0241099 A1 | 12/2004 | Popp et al. |
| 7,960,416 B2 | 6/2011 | Sato et al. | 2004/0247531 A1 | 12/2004 | Riedel et al. |
| 2001/0006654 A1 | 7/2001 | Cannell et al. | 2004/0253275 A1 | 12/2004 | Eini et al. |
| 2001/0027218 A1 | 10/2001 | Stern et al. | 2004/0258627 A1 | 12/2004 | Riedel et al. |
| 2001/0027981 A1 | 10/2001 | Yquel | 2004/0265240 A1 | 12/2004 | Tamarkin et al. |
| 2001/0036450 A1 | 11/2001 | Verite et al. | 2005/0002976 A1 | 1/2005 | Wu |
| 2002/0002151 A1 | 1/2002 | Ono et al. | 2005/0013853 A1 | 1/2005 | Gil-Ad et al. |
| 2002/0004063 A1 | 1/2002 | Zhang | 2005/0031547 A1 | 2/2005 | Tamarkin et al. |
| 2002/0013481 A1 | 1/2002 | Schonrock et al. | 2005/0042182 A1 | 2/2005 | Arkin et al. |
| 2002/0015721 A1 | 2/2002 | Simonnet et al. | 2005/0054991 A1 | 3/2005 | Tobyn et al. |
| 2002/0032171 A1 | 3/2002 | Chen et al. | 2005/0069566 A1 | 3/2005 | Tamarkin et al. |
| 2002/0035046 A1 | 3/2002 | Lukenbach et al. | 2005/0074414 A1 | 4/2005 | Tamarkin et al. |
| 2002/0035070 A1 | 3/2002 | Gardlik et al. | 2005/0075407 A1 | 4/2005 | Tamarkin et al. |
| 2002/0035087 A1 | 3/2002 | Barclay | 2005/0079139 A1 | 4/2005 | Jacques et al. |
| 2002/0035182 A1 | 3/2002 | L'Alloret et al. | 2005/0084551 A1 | 4/2005 | Jensen et al. |
| 2002/0039591 A1 | 4/2002 | Dahle | 2005/0085843 A1 | 4/2005 | Opolski et al. |
| 2002/0044659 A1 | 4/2002 | Ohta | 2005/0101936 A1 | 5/2005 | Gonzales et al. |
| 2002/0045659 A1 | 4/2002 | Michelet et al. | 2005/0106197 A1 | 5/2005 | Blin et al. |
| 2002/0048798 A1 | 4/2002 | Avery et al. | 2005/0123494 A1 | 6/2005 | Swaile et al. |
| 2002/0058010 A1 | 5/2002 | Picard-Lesboueyries et al. | 2005/0123496 A1 | 6/2005 | Shah et al. |
| 2002/0072544 A1 | 6/2002 | Miller et al. | 2005/0186142 A1 | 8/2005 | Tamarkin et al. |
| 2002/0090386 A1 | 7/2002 | Halswanter et al. | 2005/0186147 A1 | 8/2005 | Tamarkin et al. |
| 2002/0098215 A1 | 7/2002 | Douin et al. | 2005/0189377 A1 | 9/2005 | Lanzendorfer et al. |
| 2002/0111281 A1 | 8/2002 | Vishnupad | 2005/0196414 A1 | 9/2005 | Dake et al. |
| 2002/0117516 A1 | 8/2002 | Lasserre et al. | 2005/0205086 A1 | 9/2005 | Tamarkin et al. |
| 2002/0134376 A1 | 9/2002 | Castro et al. | 2005/0207837 A1 | 9/2005 | Kosh et al. |
| 2002/0136755 A1 | 9/2002 | Tyrrell et al. | 2005/0222090 A1 | 10/2005 | Cheng et al. |
| 2002/0143188 A1 | 10/2002 | Garvey et al. | 2005/0232869 A1 | 10/2005 | Tamarkin et al. |
| 2002/0153390 A1 | 10/2002 | Vlodek | 2005/0244342 A1 | 11/2005 | Friedman et al. |
| 2002/0165170 A1 | 11/2002 | Wilson et al. | 2005/0244354 A1 | 11/2005 | Speron |
| 2002/0182162 A1 | 12/2002 | Shahinpoor et al. | 2005/0245902 A1 | 11/2005 | Cornish et al. |
| 2002/0187181 A1 | 12/2002 | Godbey et al. | 2005/0252995 A1 | 11/2005 | Westphal et al. |
| 2002/0198136 A1 | 12/2002 | Mak et al. | 2005/0255048 A1 | 11/2005 | Hirsh et al. |
| 2003/0006193 A1 | 1/2003 | Ikeda et al. | 2005/0258189 A1 | 11/2005 | Peterson et al. |
| 2003/0031693 A1 | 2/2003 | Breton et al. | 2005/0266035 A1 | 12/2005 | Healy et al. |
| 2003/0053961 A1 | 3/2003 | Eccard | 2005/0268416 A1 | 12/2005 | Sommers |
| 2003/0077297 A1 | 4/2003 | Chen et al. | 2005/0271596 A1 | 12/2005 | Friedman et al. |
| 2003/0078172 A1 | 4/2003 | Guiramand et al. | 2005/0271598 A1 | 12/2005 | Friedman et al. |
| 2003/0114520 A1 | 6/2003 | Pereira et al. | 2005/0276836 A1 | 12/2005 | Wilson et al. |
| 2003/0118515 A1 | 6/2003 | Jew et al. | 2005/0281755 A1 | 12/2005 | Zarif et al. |
| 2003/0130247 A1 | 7/2003 | Gans et al. | 2005/0281766 A1 | 12/2005 | Martin et al. |
| 2003/0175232 A1 | 9/2003 | Elliott et al. | 2005/0285912 A1 | 12/2005 | Delametter et al. |
| 2003/0175315 A1 | 9/2003 | Yoo et al. | 2005/0287081 A1 | 12/2005 | Aust et al. |
| 2003/0180347 A1 | 9/2003 | Young et al. | 2006/0008432 A1 | 1/2006 | Scarampi et al. |
| 2003/0185839 A1 | 10/2003 | Podolsky | 2006/0018937 A1 | 1/2006 | Friedman et al. |
| 2003/0194379 A1 | 10/2003 | Brugger et al. | 2006/0018938 A1 | 1/2006 | Neubourg |

| Publication No. | Date | Inventor |
|---|---|---|
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0237724 A1 | 10/2007 | Abram et al. |
| 2007/0253911 A1* | 11/2007 | Tamarkin et al. ............... 424/43 |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1* | 12/2007 | Tamarkin et al. ............... 424/43 |
| 2007/0292359 A1 | 12/2007 | Friedman et al. |
| 2007/0292461 A1* | 12/2007 | Tamarkin et al. ............ 424/401 |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0221194 A1 | 9/2010 | Loupenok |
| 2011/0002857 A1 | 1/2011 | Tamarkin et al. |
| 2011/0002969 A1 | 1/2011 | Serraima et al. |
| 2011/0212033 A1 | 9/2011 | Tamarkin et al. |
| 2011/0268665 A1 | 11/2011 | Tamarkin et al. |

FOREIGN PATENT DOCUMENTS

| | | |
|---|---|---|
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0 156 507 | 10/1985 |
| EP | 0 186 453 | 7/1986 |
| EP | 0 211 550 | 2/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |

| | | | | | | |
|---|---|---|---|---|---|---|
| EP | 1 734 927 | 12/2006 | | JP | 9110636 | 4/1997 |
| EP | 1 758 547 | 3/2007 | | JP | 10114619 | 5/1998 |
| EP | 1 584 324 | 11/2007 | | JP | 3050289 | 9/1998 |
| EP | 1 889 609 | 2/2008 | | JP | 2010/332456 | 12/1998 |
| FR | 2 591 331 | 6/1987 | | JP | 11501045 | 1/1999 |
| FR | 2 640 942 | 6/1990 | | JP | 11250543 | 9/1999 |
| FR | 2 736 824 | 1/1997 | | JP | 2000/017174 | 1/2000 |
| FR | 2 774 595 | 8/1999 | | JP | 2000/080017 | 3/2000 |
| FR | 2 789 371 | 8/2000 | | JP | 2000/128734 | 5/2000 |
| FR | 2 793 479 | 11/2000 | | JP | 2000/191429 | 7/2000 |
| FR | 2 814 959 | 4/2002 | | JP | 2000/239140 | 9/2000 |
| FR | 2 833 246 | 6/2003 | | JP | 2000/351726 | 12/2000 |
| FR | 2 840 903 | 12/2003 | | JP | 2000/354623 | 12/2000 |
| FR | 2 843 373 | 2/2004 | | JP | 2001/002526 | 1/2001 |
| FR | 2 845 672 | 4/2004 | | JP | 2001/019606 | 1/2001 |
| FR | 2 848 998 | 6/2004 | | JP | 2001/072963 | 3/2001 |
| FR | 2 860 976 | 4/2005 | | JP | 2002/012513 | 1/2002 |
| FR | 2 915 891 | 11/2008 | | JP | 2002/047136 | 2/2002 |
| GB | 808 104 | 1/1959 | | JP | 2002/524490 | 8/2002 |
| GB | 808 105 | 1/1959 | | JP | 2002/302419 | 10/2002 |
| GB | 922 930 | 4/1963 | | JP | 03/012511 | 1/2003 |
| GB | 933 486 | 8/1963 | | JP | 2003/055146 | 2/2003 |
| GB | 998 490 | 7/1965 | | JP | 2004/047136 | 2/2004 |
| GB | 1 026 831 | 4/1966 | | JP | 2004/250435 | 9/2004 |
| GB | 1 033 299 | 6/1966 | | JP | 2004/348745 | 12/2004 |
| GB | 1 081 949 | 9/1967 | | JP | 2005/314323 | 11/2005 |
| GB | 1 121 358 | 7/1968 | | JP | 2005/350378 | 12/2005 |
| GB | 1 162 684 | 8/1969 | | JP | 2006/008574 | 1/2006 |
| GB | 1 170 152 | 11/1969 | | JP | 2006/036317 | 2/2006 |
| GB | 1 201 918 | 8/1970 | | JP | 2006/103799 | 4/2006 |
| GB | 1 347 950 | 2/1974 | | JP | 2006525145 | 11/2006 |
| GB | 1 351 761 | 5/1974 | | JP | 2007/131539 | 5/2007 |
| GB | 1 351 762 | 5/1974 | | JP | S48-92282 | 12/2007 |
| GB | 1 353 381 | 5/1974 | | KR | 143232 | 7/1998 |
| GB | 1 376 649 | 12/1974 | | KR | 2001/003063 | 1/2001 |
| GB | 1 397 285 | 6/1975 | | RU | 2277501 | 6/2006 |
| GB | 1 408 036 | 10/1975 | | UA | 66796 | 6/2004 |
| GB | 1 457 671 | 12/1976 | | WO | 82/01821 | 6/1982 |
| GB | 1 489 672 | 10/1977 | | WO | 86/05389 | 9/1986 |
| GB | 2 004 746 | 4/1979 | | WO | 88/01502 | 3/1988 |
| GB | 1 561 423 | 2/1980 | | WO | 88/01863 | 3/1988 |
| GB | 2 114 580 | 8/1983 | | WO | 88/08316 | 11/1988 |
| GB | 2 153 686 | 8/1985 | | WO | 89/06537 | 7/1989 |
| GB | 2 172 298 | 9/1986 | | WO | 90/05774 | 5/1990 |
| GB | 2 206 099 | 12/1988 | | WO | 91/11991 | 8/1991 |
| GB | 2 166 651 | 5/1996 | | WO | 92/00077 | 1/1992 |
| GB | 2 337 461 | 11/1999 | | WO | 92/05142 | 4/1992 |
| GB | 2 367 809 | 4/2002 | | WO | 92/05763 | 4/1992 |
| GB | 2 406 330 | 3/2005 | | WO | 92/11839 | 7/1992 |
| GB | 2 406 791 | 4/2005 | | WO | 93/25189 | 12/1993 |
| IL | 49491 | 9/1979 | | WO | 94/06440 | 3/1994 |
| IL | 152 486 | 5/2003 | | WO | 96/03115 | 2/1996 |
| JP | 60001113 | 4/1978 | | WO | 96/19921 | 7/1996 |
| JP | 55069682 | 5/1980 | | WO | 96/24325 | 8/1996 |
| JP | 57044429 | 3/1982 | | WO | 96/26711 | 9/1996 |
| JP | 56039815 | 4/1984 | | WO | 96/27376 | 9/1996 |
| JP | 61275395 | 12/1986 | | WO | 96/39119 | 12/1996 |
| JP | 62241701 | 10/1987 | | WO | 97/03638 | 2/1997 |
| JP | 63119420 | 5/1988 | | WO | 97/39745 | 10/1997 |
| JP | 1100111 | 4/1989 | | WO | 98/17282 | 4/1998 |
| JP | 1156906 | 6/1989 | | WO | 98/18472 | 5/1998 |
| JP | 2184614 | 7/1990 | | WO | 98/19654 | 5/1998 |
| JP | 2255890 | 10/1990 | | WO | 98/21955 | 5/1998 |
| JP | 4282311 | 10/1992 | | WO | 98/23291 | 6/1998 |
| JP | 4312521 | 11/1992 | | WO | 98/36733 | 8/1998 |
| JP | 5070340 | 3/1993 | | WO | 98/52536 | 11/1998 |
| JP | 5213734 | 8/1993 | | WO | 99/08649 | 2/1999 |
| JP | 6100414 | 4/1994 | | WO | 99/20250 | 4/1999 |
| JP | H06-263630 | 6/1994 | | WO | 99/37282 | 7/1999 |
| JP | 6329532 | 11/1994 | | WO | 99/53923 | 10/1999 |
| JP | 2007/155667 | 6/1995 | | WO | 00/09082 | 2/2000 |
| JP | 7215835 | 8/1995 | | WO | 00/15193 | 3/2000 |
| JP | 2008/040899 | 2/1996 | | WO | 00/23051 | 4/2000 |
| JP | 8501529 | 2/1996 | | WO | 00/33825 | 6/2000 |
| JP | 8119831 | 5/1996 | | WO | 00/38731 | 7/2000 |
| JP | 8165218 | 6/1996 | | WO | 00/61076 | 10/2000 |
| JP | 8277209 | 10/1996 | | WO | 00/76461 | 12/2000 |
| JP | 09 084855 | 3/1997 | | WO | 01/05366 | 1/2001 |
| JP | 9099553 | 4/1997 | | WO | 01/08681 | 2/2001 |

| | | |
|---|---|---|
| WO | 01/10961 | 2/2001 |
| WO | 01/53198 | 7/2001 |
| WO | 01/54212 | 7/2001 |
| WO | 01/54679 | 8/2001 |
| WO | 01/62209 | 8/2001 |
| WO | 01/70242 | 9/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | 02/00820 | 1/2002 |
| WO | 02/15860 | 2/2002 |
| WO | 02/15873 | 2/2002 |
| WO | 02/28435 | 4/2002 |
| WO | 02/41847 | 5/2002 |
| WO | 02/43490 | 6/2002 |
| WO | 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | 2007/012977 | 2/2007 |
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | 2007/085899 | 8/2007 |
| WO | 2007/085902 | 8/2007 |
| WO | 2007/099396 | 9/2007 |
| WO | 2007/111962 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | 2009/098595 | 8/2009 |
| WO | 2011/039637 | 4/2011 |
| WO | 2011/039638 | 4/2011 |

OTHER PUBLICATIONS

"Minocycline" accessed on Ocotober 21, 2011 at en.wikipedia.org/wiki/Minocycline, 7 pages.

"Reaction Rate" Accessed at en.wikipedia.org/wiki/Reaction_rate on Dec. 18, 2011, 6 pages.

'Niram Chemicals' [online] Niram Chemicals, [retrieved on Jul. 17, 2012]. Retrieved from the Internet: <URL: http://www.indiamart.com/niramchemicals/chemicals.html>, 7 pages.

'Surfactant' [online]. Wikipedia, 2010, [retrieved on Oct. 24, 2010]. Retrieved from the Internet: <URL: http://en.wikipedia.org/wiki/Surfactant>, 7 pages.

Adachi, Shuji. "Storage and Oxidative Stability of O/W/ Nano-emulsions." Foods Food Ingredients. J. Jpn. vol. 209, No. 11. 2004. 1 page.

Alcohol SDA 40B.http://www.pharmco-prod.com/pages/MSDS/SDA.sub.--40B.sub.--200.pdf Accessed Dec. 9, 2008, 2 pages.

Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds,"Antimicrobial Agents and Chemotherapy, vol. 35, No. 9, pp. 1799-1803, 1991.

Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.

Arct et al., "Common Cosmetic Hydrophilic Ingredients as Penetration Modifiers of Flavonoids", International Journal of Cosmetic Science, 24(6):357-366 (2002)—Abstract, 1 page.

Arisan, http://www.arisankimya.com/kozmetik.htm Accessed Dec. 10, 2008, 8 pages.

Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Barry and Badal, "Stability of minocycline, doxycycline, and tetracycline stored in agar plates and microdilution trays," *Current Microbiology*, 1978, 1:33-36.

Barry, B.W. et al, Comparative bio-availability and activity of proprietary topical corticosteroid preparations: vasoconstrictor assays on thirty-one ointments, British Journal of Dermatology, 93, 563-571, 1975.

Benet, et al., Application of NMR for the Determination of HLB Values of Nonionic Surfactants, Journal of the American Oil Chemists Society, vol. 49, 1972, 499-500.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfactants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; http://www.sciencelab.com/xMSDS-Polyethylene.sub.--glycol.sub.--1000-9926-622. Accessed Dec. 13, 2008, 6 pages.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

D.W.A. Sharp Dictionary of Chemistry, Penguin Books, 1983, 3 pages.

Dalby, "Determination of Drug Solubility in Aerosol Propellants," Pharmaceutical Research, vol. 8, No. 9, 1991, pp. 1206-1209.

Dawber, et al., "Hypertrichosis in Females Applying Minoxidil Topical Solution and in Normal Controls", JEADV, 17:271-275 (2003).

Denatonium Benzoate http://www.newdruginfo.com/pharmaceopeia/usp28/v28230/usp28nf23s0.sub.--m-22790.htm Accessed Dec. 9, 2008, 2 pages.

Dentinger, et al., "Stability of Nifedipine in an Extemporaneously Compounded Oral Solution", American Journal of Health-System Pharmacy, 60(10):1019-1022 (2003)—Abstract, 1 page.

Disorder. (2007). In the American Heritage Dictionary of the English Language. Retrieved from http://www.credoreference.com/entry/hmdictenglang/disorder. 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Load). Aug. 2006; 111(2): 145-51.

Edwards, "Imiquimod in Clinical Practice", J. Am Acad Dermatol., 43(1, Pt 2):512-517 (2000)—Abstract, 1 page.

Emulsifiers with HLB values. http://www.theherbarie.com/files/resources-center/formulating/Emulsifiers-.sub.--HLB.sub.--Values.pdf accessed Aug. 5, 2009 (3 pps).

Encyclopedia of Pharmaceutical Technology, Second Edition, vol. 3, Copyright 2002, 4 pages.

Esposito, E. et al. "Nanosystems for Skin Hydration: A Comparative Study." International Journal of Cosmetic Science. 29. 2007. pp. 39-47.

Ethanol, Accessed http://www.sigmaaldrich.com/catalog/ProductDetail.do?N4=E7023SIAL&N5=SEAR-CH.sub.--CONCAT.sub.--PNOBRAND.sub.--KEY&F=SPEC Dec. 9, 2008, 2 pages.

Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Flick, Cosmetic and Toiletry Formulations, vol. 5, 2nd Edition, Copyright 1996, 63 pages. Relevant pp. 251-309.

Fontana, Anthony J., "Water Activity: Why it is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Galligan, John et al., "Adhesive Polyurethane Liners for Anterior Restorations," J. Dent. Res., Jul.-Aug. 1968, pp. 629-632.

Gelbard et al. "Primary Pediatric Hyperhidrosis: A Review of Current Treatment Options." Pediatric Dermatology. 2008. 25 (6). pp. 591-598.

Gill, A.M, et al., "Adverse Drug Reactions in a Paediatric Intensive Care Unit," Acta Paediatr 84:438-441, 1995.

Gladkikh, "Ascorbic Acid and Methods of Increasing its Stability in Drugs", Translated from Khimiko-Farmatsevticheskii Zhurnal, 4(12):37-42 (1970)—1 page.

Glaser, et al., Hyperhidrosis: A Comprehensive and Practical Approach to Patient Management, Expert Rev. Dermatol. 1(6), 773-775 (2006).

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Gschnait, F., et al., "Topical Indomethacin Protects from UVB and UVA Irriadiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, No. 2, pp. 155-161.

Hall, Karla, "Diaper Area Hemangiomas: A Unique Set of Concerns," http://members.tripod.com/.about.Michelle.sub.--G/diaper.html, Dec. 1, 2008, 8 pages.

Hallstar. Retrieved online on Jun. 4, 2011. <URL:http://www.hallstar.com/pis.php?product=1H022>. 1 page.

Hargreaves, "Chemical Formulation, An Overview of Surfactant-Based Preparations Used in Everyday Life", *The Royal Society of Chemistry*, pp. 114-115 (2003).

Harrison, et al., "Effects of cytokines and R-837, a cytokine inducer, on UV-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Hashim, et al. "Tinea versicolor and visceral leishmaniasis," Int J Dermatol., Apr. 1994; 33(4), pp. 258-259 (abstract only).

Heart Failure, The Merck Manual, 2008 <<http://www.merck.com/mmhe/sec03/ch025/ch025a.html>> 12 pages.

Hepburn, NC., "Cutaneous leishmaniasis," Clin Exp Dermatol, Jul. 2000; 25(5), pp. 363-370 (abstract only).

Hill, Randall M. (Ed.) Silicone Surfactants, Table of Contents and Chapter 7, "Silicone Surfactants: Applicants in the Personal Care Industry," by David T. Floyd, 1999 (30 Pages).

Hormones. Http://www.greenwillowtree.com/Page.bok?file=libido. html. Jan. 2001.

http://ibabydoc.com/online/diseaseeczema.asp., Atopic Dermatitis, Copyright 2000, 6 pages.

http://web.archive.org/web/20000106225413/http://pharmacy. wilkes.edu/kibbeweb/lab7.html, Characteristics of Surfactants and Emulsions, Jan. 29, 2010, 5 pages.

http://www.agworkshop.com/p3.asp, AG&Co. Essential oil workshop. 1 page. Accessed Jan. 31, 2010.

Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.

Hydroxyethylcellulose. Http: //terpconnect.umd.edu/-choi/MSDS/Sigma-Aldrich/HYDROXYETHYL%2OCELLULOSE, 5 pages, Jan. 14, 2004.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03. net/com/oxymatrine/down/1249534834.pdf>. Aug. 15, 2009. 3 pages.

Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

Izquierdo, P. et al. "Formation and Stability of Nano-Emulsions Prepared Using the Phase Inversion Temperature Method." University of Barcelona. Sep. 17, 2001. 1 page.

Jan. "Troubled Times: Detergent Foam." http://zetatalk.com/health/theall7c.htm. Accessed Feb. 9, 2012. 2 pages.

Joseph, "Understanding foams & foaming," University of Minnesota (1997), at http://www.aem.umn.edu/people/faculty/joseph/archive/docs/understandingfoams.pdf, pp. 1-8.

Kalkan, et al., The Measurement of Sweat Intensity Using a New Technique, Tr. J. of Medical Sciences 28, 515-517 (1998).

Kanamoto, et al., "Pharmacokinetics of two rectal dosage forms of ketoprofen in patients after anal surgery," J Pharmacobiodyn., Mar. 1988; 11(3):141-5.

Kang,et al., "Enhancement of the Stability and Skin Penetration of Vitamin C by Polyphenol", Immune Netw., 4(4):250-254 (2004)—Abstract, 1 page.

Karasu, T.B. et al., "Treatment of Patients with Major Depressive Disorder, Second Edition," pp. 1-78, 2000.

Kathon.TM. CG (product information sheet by Rohm and Haas, Jun. 2006).

Kim, "Stability of Minoxidil in Aqueous Solution", Yakhak Hoechi, 30(5):228-231 (1986)—Abstract, 1 page.

Kinnunen, "Skin reactions to hexylene glycol," Contact Dermatitis Sep. 1989; 21(3): 154-8.

Kleber, M.D., H.D. et al., "Treatment of Patients with Substance Use Disorders, Second Edition," pp. 1-276, 2006.

Koerber, S., "Humectants and Water Activity," Water Activity News, 2000, ISSN No. 1083-3943.

Kreuter, J. "Nanoparticles and microparticles for drug and vaccine delivery," J. Anat. (1996) 189, pp. 503-505.

Kumar, J. et ak., "Application of Broad Spectrum Antiseptic Povidone Iodine as Powerful Action: A Review," Journal of Pharmaceutical Science and Technology vol. 1(2), 2009, 48-58.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." *J Am. Acad. Dermatol*. 45:487-498. Oct. 2001.

Lebwohl et al., "A randomized, double-blind, placebo-controlled study of clobestasol propionate 0.05% foam in the treatment of nonscalp psoriasis," *International Journal of Dermatology*, 2002, 41(5): 269-274.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Leung, et al., "Bioadhesive Drug Delivery in Water-Soluble Polymers," American Chemical Society, Chapter 23, 1991, pp. 350-366.

Li, et al., "Solubility Behavior of Imiquimod in Alkanoic Acids", Abstract 3029, Pharmaceutical Research, vol. 14, No. 11 Supplemental (November), p. S475 (1997), 2 pages.

Licking Vaginal Dryness without a Prescription. Accessed http://www.estronaut.com/a/vag.sub.--dryness.htm on Dec. 14, 2008, 3 pages.

Lippacher, A. et al. "Liquid and Semisolid SLN Dispersions for Topical Application" Rheological Characterization. European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Martindale, The extra pharmacopoeia [28th] edition, Eds.: Reynolds, J.E.F. and Prasad, A.B., The Pharmaceutical Press, London, pp. 862-864, 1982.

Martindale. 33 ed. London, Bath Press, 2002. pp. 1073 and 1473.

Material Safety Data Sheet, Progesterone, Apr. 26, 2006, 5 pages.

Material Safety Data Sheet, Science Lab.com, Polyethylene Glycol 1000, MSDS, Nov. 6, 2008, 6 pages.

Merck index, 10th edition, Merck & Co., Inc.: Rahway, NJ, 1983, pp. 39 (entry 242 for allantoin).

Merck index, 14th edition, O'Neill, ed., 2006, entry for p-amino benzoic acid.

Merck index, 14th edition, O'Neill, ed., 2006, entry for zinc oxide.

Merck Index, An Encyclopedia of Chemicals, Drugs, and Biologicals. 13$^{th}$ Edition. O'Neil et al eds. Entries 1058, 2350, 6143, and 8803. 2001. 7 pages.

Merck Manual Home Edition. "Excessive Sweating: Sweating Disorders." Accessed Apr. 14, 2011 at www.merckmanuals.com/home/print/sec18/ch206/ch206c.html. 2 pages.

Merriam Webster Online Dictionary [online] retrieved from http://www.merriam-webster.com/cgi-bin/dictionary?book=dictionary &va=derivative on Jul. 5, 2008; 1 page.

Merriam-Webster Online Dictionaary, 2008, "Mousse," Merriam-Webster Online, Dec. 8, 2008 http://www.merriam-webster.com/dictionary/mousse, 2 pages.

Messenger, et al., "Minoxidil: Mechanisms of Action on Hair Growth", British Journal of Dermatology, 150:186-194 (2004).

Metronidazole. www.usp.org/pdf/EN/veterinary/metronidazole.pdf. accessed Sep. 10, 2009, 4 pages.

Metz, et al., "A Phase I Study of Topical Tempol for the Prevention of Alopecia Induced by Whole Brain Radiotherapy", Clinical Cancer Research, 10:6411-6417 (2004).

Meucci, et al., "Ascorbic Acid Stability in Aqueous Solutions", Acta Vitaminol Enzymol, 7(3-4):147-153 (1985)—Abstract, 1 page.

MMP Inc. International Development and Manufacturing, "Formulating specialities," http://mmpinc.com, 3 pages. Feb. 2, 2010.

Molan, Peter Clark, "World Wide Wounds," Dec. 2001, 13 pages.

Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.

Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.

Nietz, "Molecular orientation at surfaces of solids," J. Phys. Chem., 1928, 32(2): 255-269.

No Author Listed. "Opitmization of Nano-Emulsions Production by Microfluidization." European Food Research and Technology. vol. 225, No. 5-6. Sep. 2007. Abstract. 1 page.

Office Action for U.S. Appl. No. 11/430,437, Tamarkin et al., May 9, 2008, 27 pages.

Office Action received from the U.S. Patent Office, U.S. Appl. No. 11/430,599, Jul. 28, 2008 (59 pages).

Oil. Dictionary of Chemistry. Editor: DWA Sharp. Copyright 1990.

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

OM Cinnamate. http://www.makingcosmetics.com/sunscreens/OM-Cinnamate-p102.html accessed Sep. 26, 2009, 1 page.

Padhi et al., "Phospho-olicines as positive-electrode materials for rechargeable lithium batteries," J. Electrochemical Soc., 1997, 144(4): 1188-1194.

Pakpayat, et al., "Formulation of Ascorbic Acid Microemulstions with Alkyl Polyglycosides", European Journal of Pharmaceutics and Biopharmaceutics, 72:444-452 (2009).

Paula. http://ww.cosmeticscop.com/cosmetic-ingredient-dictionary/definition/259/c12-15-alkyl-benzoate.aspx. Printed Oct. 24, 2010. 1 page.

Pendergrass, "The shape and dimension of the human vagina as seen in three-dimensional vinyl polysiloxane casts," Gynecol Obstet. Invest. 1996:42(3):178-82.

Prescription Information for Aldara, Mar. 2007 (29 pages).

Prevent. (2007). In the American Heritage Dictionary of the English Language. Retrieved from http://www.credoreference.com/entry/hmdictenglang/prevent. 1 page.

Psoriasis, http://www.quickcare.org/skin/causes-of0psoriasis.html. Accessed Sep. 9, 2010—3 pages.

Purcell, Hal C. "Natural Jojoba Oil Versus Dryness and Free Radicals." Cosmetics and Toiletries Manufacture Worldwide. 1988. 4 pages.

Raschke, et al., "Topical Activity of Ascorbic Acid: From In Vitro Optimization to In Vivo Efficacy", Skin Pharmacology and Physiology, 17(4):200-206 (2004)—Abstract, 1 page.

Ravet et al., "Electroactivity of natural and synthetic triphylite," J. of Power Sources, 2001, 97-98: 503-507.

Raymond, Iodine as an Aerial Disinfectant, Journal of Hygiene, vol. 44, No. 5 (May 1946), pp. 359-361.

Receptacle. Merriam Webster. Http://www.merriam-webster.com/dictionary/receptacle. Accessed Jul. 12, 2011. 1 page.

Richwald, "Imiquimod", Drugs Today, 35(7):497 (1999)—Abstract, 1 page.

Rieger and Rhein. "Emulsifier Selection/HLB." Surfactants in Cosmetics. 1997 (no month given). 1 page.

Rosacea, http://clinuvel.com/skin-conditions/common-skin-conditions/rosacea#h0-6-prevention. Accessed Sep. 9, 2010, 5 pages.

Savin, et al., "Tinea versicolor treated with terbinafine 1% solution," Int J. Dermatol, Nov. 1999; 38(11), pp. 863-865.

Schmidt A., "*Malassezia furfur*: a fungus belonging to the physiological skin flora and its relevance in skin disorders," Curtis., Jan. 1997; 59(1), pp. 21-24 (abstract).

Schutze, M.D., Harry "Iodine and Sodium Hypochlorite as Wound Disinfectants," The British Medical Journal, pp. 921-922, 1915.

Scientific Discussion for the approval of Aldara, EMEA 2005 (10 pages).

Scott as Published in Pharmaceutical Dosage Forms; Disperse Systems, vol. 3, Copyright 1998, 120 pages.

Seborrheic Dermatitis, http://www.cumc.columbia.edu/student/health/pdf/R-S/Seborrhea%20Dermatitis.pdf. Access Sep. 9, 2010, 2 pages.

Shear, et al., "Pharmacoeconomic analysis of topical treatments for tinea infections," Pharmacoeconomics. Mar. 1995; 7(3); pp. 251-267 (abstract only).

Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.

Shim, et al., "Transdermal Delivery of Mixnoxidil with Block Copolymer Nanoparticles", J. Control Release, 97(3):477-484 (2004)—Abstract, 1 page.

Sigma Aldrich, "HLB-Numbers in Lithography Nanopatterning," http://www.sigmaaldrich.com/materials-science/micro-and-nanoelectronics/1-ithography-nanopatterning/hlb-numbers.html, accessed: Feb. 2, 2009, pp. 1-3.

Sigma-Aldrich, Material Safety Data Sheet, Hydroxyethyl Cellulose, Mar. 3, 2004, 5 pages.

Silicone. Definition. Retrieved Apr. 19, 2011 from http://www.oxforddictionaries.com/definition/silicone?view=uk. 1 page.

Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.

Skin Biology, CP Serum—Copper-Peptide Serum for Skin Regeneration and Reducing Wrinkles, Skin Biology, http;//web.archive.org/web/20030810230608/http://www.skinbio.com/cpserum.-html, Dec. 1, 2008, 21 pages.

Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 3pages.

Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.

Sonneville-Aubrun, O. et al. "Nanoemulsions: A New Vehicle for Skincare Products." Advances in Colloid and Interface Science. 108-109.. 2004. pp. 145-149.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).

Sreenivasa, et al., "Preparation and Evaluation of Minoxidil Gels for Topical Application in Alopecia", Indian Journal of Pharmaceutical Sciences, 68(4):432-436 (2006), 11 pages.

Stehle et al., Uptake of minoxidil from a new foam formulation devoid of propylene glycol to hamster ear hair follicles, J. Invest. Dermatol., 2005, 124(4), A101.

Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.

Surfactant. Chemistry Glossary. Http://chemistry.about.com/od/chemistryglossary/g/surfactant.htm, 2012, 1 page.

Sweetman, Sean C. Martindale: The Complete Drug Reference. 33rd Edition. London. Pharmaceutical Press. Jun. 21, 2002. pp. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Tanhehco, "Potassium Channel Modulators as Anti-Inflammatory Agents", Expert Opinion on Therapeutic Patents, 11(7):1137-1145 (2001)—Abstract, 3 pages.

Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16 (Abstract only).

Tata, et al., "Penetration of Minoxidil from Ethanol Propylene Glycol Solutions: Effect of Application Volume on Occlusion", Journal of Pharmaceutical Sciences, 84(6):688-691 (1995).

Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb 4, 2009, 4 pages.
Tones-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
Yamada and Chung, "Crystal Chemistry of the Olivine-Type Li($Mn_yFe_{1-y}$)$PO_4$ and ($Mn_yFe_{1-y}$)$PO_4$ as Possible 4 V Cathode Materials for Lithium Batteries," J. Electrochemical Soc., 2001, 148(8): A960-967.
"Coal tars and coal-tar pitches," *Report on Carcinogens, Twelfth Edition*, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *DARU*, 2003, 11(1):19-22.

Effendy and Maibach. "Surfactants and Experimental Irritant Contact Dermatitus." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluhr et al., "Glycerol accelerates recovery of barrier function in vivo," *Acta Derm. Venereol.*, 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990.
Hwang et al. "Isolation and identification of mosquito repellents in *Artemisia vulgaris*," *J. Chem. Ecol.*, 11: 1297-1306, 1985.
Knight et al., "Topical diltiazem ointment in the treatment of chronic anal fissure," *Br. J. Surg.*, 2001, 88(4):553-6.
Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic.*, 1986, 24:495-196.
Osborne and Henke, "Skin Penetration Enhancers Cited in the Technical Literature," *Pharm. Technology*, Nov. 1997, pp. 58-86.
Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.
Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.

Van Cutsem et al., "The antiinflammatory efects of ketoconazole," *J. Am. Acad. Dermatol.*, 1991, 25(2 pt 1):257-261.

Wang and Chen, "Preparation and surface active properties of biodegradable dextrin derivative surfactants," *Colloids and Surfaces A: Physicochemical and Engineering Aspects*, 2006, 281(1-3):190-193.

Weindl et al., "Hyaluronic acid in the treatment and prevention of skin diseases: molecular biological, pharmaceutical and clinical aspects," *Skin Pharmacology and Physiology*, 2004, 17: 207-213.

Xynos et al., "Effect of nifedipine on rectoanal motility," *Dis Colon Rectum*, 1996, 39(2):212-216.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No. 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. "Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

International Preliminary Report on Patentability from PCT/IB2009/007184, dated Apr. 12, 2011, and International Search Report, dated May 3, 2010, 9 pages.

\* cited by examiner

OIL-BASED FOAMABLE CARRIERS AND FORMULATIONS

CROSS REFERENCE TO RELATED APPLICATIONS

This application is the National Stage under 35 U.S.C. §371(c) of International Application No. PCT/IB2009/007184, filed Oct. 6, 2009, entitled "Oil-Based Foamable Carriers and Formulations," which claims the benefit of priority under 35 U.S.C. §119(e) of U.S. Provisional Patent Application No. 61/103,500, filed on Oct. 7, 2008, entitled "Oil and Liquid Silicone Carriers and Formulations for External and Body Cavity Application of Active Agents and Uses Thereof," and U.S. Provisional Patent Application No. 61/120,842, filed on Dec. 8, 2008, entitled "Oil-Based Foamable Carriers and Formulations," which are herein incorporated by reference in their entireties.

This application is a continuation-in-part of and claims the benefit of priority under 35 U.S.C. §120 of co-pending U.S. patent application Ser. No. 12/795,164, filed Jun. 7, 2010, entitled "Carriers, Formulations, Methods for Formulating Unstable Active Agents for External Application and Uses Thereof," which is a continuation of International Application No. PCT/IB2008/003932, filed Dec. 8, 2008, entitled "Carriers, Formulations, Methods for Formulating Unstable Active Agents for External Application and Uses Thereof," which claims the benefit of priority under 35 U.S.C. §119(e) of U.S. Provisional Patent Application No. 61/012,414, filed Dec. 7, 2007, entitled "Carriers, Formulations, Methods for Formulating Unstable Active Agents for External Application and Uses Thereof," and U.S. Provisional Patent Application No. 61/103,500, filed Oct. 7, 2008, entitled "Oil and Liquid Silicone Carriers and Formulations for External and Body Cavity Application of Active Agents and Uses Thereof," which are herein incorporated by reference in their entireties.

This application is a continuation-in-part of and claims the benefit of priority under 35 U.S.C. §120 of co-pending U.S. patent application Ser. No. 12/795,213, filed Jun. 7, 2010, entitled "Oil and Liquid Silicone Foamable Carriers and Formulations," which is a continuation of International Application No. PCT/IB2008/003939, filed Dec. 8, 2008, entitled "Oil and Liquid Silicone Foamable Carriers and Formulations," which claims the benefit of priority under 35 U.S.C. §119(e) of U.S. Provisional Patent Application No. 61/103,500, filed Oct. 7, 2008, entitled "Oil and Liquid Silicone Foamable Carriers and Formulations for External and Body Cavity Application of Active Agents and Uses Thereof," and U.S. Provisional Patent Application No. 61/012,414, filed Dec. 7, 2007, entitled "Carriers, Formulations, Methods for Formulating Unstable Active Agents for External Application and Uses Thereof," which are herein incorporated by reference in their entireties.

FIELD

This invention relates to waterless foam formulations, specifically single phase foamable carriers. The invention further relates to methods for formulating stable and unstable active agents in topical compositions, which are suitable, inter alia, for applying to the skin or to mucosal surfaces or in body cavities and can be used for treating topical, mucosal, body cavity and/or systemic disorders in mammals. The invention further relates to vehicles which are suitable, inter alia, for delivery for a wide range of active pharmaceutical and cosmetic agents and methods for their use.

BACKGROUND

External topical administration is an important route for the administration of drugs in both systemic and topical disease treatment. For example, diseases of the skin, such as inflammatory diseases (e.g., acne), rashes, infection (e.g., microbial infection and parasitic infestation), and immune system reactions leading to rashes and/or infection, are typically treated via topical administration of a pharmaceutical active agent. Many drugs that may be useful for topical administration (e.g., antibiotics, anti-fungal agents, anti-inflammatory agents, anesthetics, analgesics, anti-allergic agents, corticosteroids, retinoids and anti-proliferative medications) are administered in hydrophobic media, such as a petrolatum-based ointment, due to their increased stability in hydrophobic solvents. While the use of stabilizers, anti oxidants antimicrobial preservatives, buffers and the like in aqueous carriers and creams to protect active or cosmetic agents is known, there are still disadvantages to formulating certain active agents in aqueous carriers, or even in carriers containing low amounts of polar solvents such as water (e.g., water in oil emulsions). For example, some active agents are known to be generally unstable or susceptible to isomerisation or to breakdown in the presence of water, resulting in loss of activity.

However, hydrophobic formulations, in particular ointments, also pose disadvantages to topical administration. For example, ointments often form an impermeable barrier. In the treatment of a topical wound, such a barrier can prevent the removal or draining of metabolic products and excreta from these wounds. Moreover, the efficacy of drugs formulated in ointments is compromised because of the difficulty for an active drug dissolved in an ointment-based carrier to pass through the barrier layer into the wound tissue. In addition, ointments (and also creams) often do not create an environment for promoting respiration of wound tissue or normal respiration of the skin. An additional disadvantage of ointment formulations is the greasy feeling left following their topical application onto the skin, mucosal membranes and wounds.

Formulations based on hydrophobic media are by their nature greasy materials and can be difficult to formulate particularly into a topical foamable composition free of lower short chain alcohols that can deliver a substantially uniform and stable composition or foam that ameliorates or overcomes the look and feel of a greasy material, especially where that composition is waterless or substantially so.

Foamable carriers offer advantages over ointments and creams for topical administration of pharmaceuticals. While hydrophobic foamable carriers are known, it is far from simple or obvious to produce hydrophobic waterless foamable carriers that when released produce foams of quality suitable for pharmaceutical or cosmetic application. An additional difficulty to be overcome, is how to adapt the formula and achieve a uniform formulation, which can accept a range of various active pharmaceutical and cosmetic agents such that the composition and active agent are stable and that the foam produced remains of quality. Specifically, one of the challenges in preparing such waterless or substantially waterless foamable compositions is ensuring that the active pharmaceutical or therapeutic agent does not react, isomerize or otherwise break down to any significant extent during is storage and use.

In general terms, it is believed that foam formed from hydrophobic waterless or substantially waterless carriers is inherently less firm or inherently weaker than water based emulsion carriers.

An aerosol product containing an oily composition containing at least one oil, and at least one hydrocarbon compound (notably, a paraffin or a fatty acid amide) having a melting point greater than or equal to 30° C. (i.e., a solid at room temperature) is known in the prior art, the compound being in the form of solid particles and one or more propellants. However, hydrocarbon solid particles were required to provide a fine bubble, stable foam.

Foams are complex dispersion systems which do not form under all circumstances. Slight shifts in foam composition, such as by the addition of active ingredients, may destabilize the foam. Foams are very complex and sensitive systems and are not formed at will. Mere addition of basic ingredients like oil, surfactant and propellant is far from sufficient to produce foams of quality that are homogenous, stable, breakable upon mechanical force and can be used to provide a shelf stable pharmaceutical or cosmetic composition. Small deviations may lead to foam collapse. Much consideration needs to be given to facilitate the introduction of an active agent, such as examining compatibility and non reactivity with the various excipients and container and determining shelf life chemical stability.

Neubourg (US 2006/0099151), for example, notes that the stability of foam is strongly dependent on the specific composition of the foam forming components, so that even small deviations in the composition may lead to a collapse of the foam. Gordon et al. (U.S. Pat. No. 3,456,052) also teaches that one cannot generate a good quality foam by simply adding a propellant to a mixture of components:

The term "foam" is a general term that encompasses a range of substances. Accordingly, the context in which "foam" is discussed must be examined carefully. The type and quality of the foam is of critical importance. There are many different types of foams and within each foam type there are many levels of qualities. For example, the froth on the head of beer, lather of shampoo, and lather of shaving cream have been loosely described as foam but all are different from one another. At one end of the cosmetic or pharmaceutical foam spectrum the foam can be long lasting and essentially not readily breakable like shaving foams. At the other end of the spectrum the foam can be quick breaking and collapses upon release.

Thermolabile foams are an example of type of quick breaking foam. They can contain significant amounts of thermolabile substances that aid their collapse upon being exposed to an increased temperature for example when applied to a body surface at 37° C. Upon being exposed to the higher temperature they collapse rapidly. Examples are foam formulations that comprise significant amounts of volatile solvents.

Breakable foam is a specialized type of foam. It is a low density foam that is stable on release at least in the short time span of several minutes, which facilitates application to a target area; but can break readily upon the application of shear force such as gentle rubbing to spread easily over a target surface. It is not thermolabile (and does not melt at skin temperature) and nor does it display late or long delayed expansion over minutes.

Some foams expand slowly whilst others do so quickly. Some foams foam immediately and some demonstrate delayed foaming. Some require mechanical lathering and some expulsion by propellant. Whilst they all fall under the so called term "foam" and may appear to have some common ingredients the results and properties of these products are different.

A suitable foamable formulation for a particular application may present challenges at several levels. For example, a foam formulation may require a stable pre foam formulation; a stable pre foam propellant formulation and ultimately delivery an effective measured amount of active agent to a target. Each of these objectives poses its own unique challenges.

The pharmaceutical and cosmetic foams discussed herein are generated in general terms by manufacturing a suitable foamable carrier composition and loading the carrier in a pressurized valved canister with an appropriate propellant. Upon expelling the canister contents a foam can be released. The type, nature and quality of the foam depends inter alia on the carrier composition, the active agent, the propellant and the method of manufacture and storage. Making a stable (physically and chemically) formulation that can be stored in a canister with a propellant that remains stable and can produce a breakable foam of quality on release is far from trivial.

An additional difficulty frequently encountered with propellant foams is their inability to dispense a uniform application of the medically active ingredient throughout the use of the entire aerosol container. This is particularly due to the fact that the active material is not stably dispersed in the foamable composition so that it will have a tendency to settle to the bottom. Further, the dispersed material will sometimes clog the spray dispensing valve to further interfere with the uniform dispensing of the medicament.

SUMMARY

There are provided improved, easy to use, stable and non-irritating oil-based foam carriers, with unique physical, therapeutic or beneficial properties having the ability to act as a vehicle for a stable or stabilized active pharmaceutical or cosmetic agent. Moreover, there are provided oil-based waterless and substantially waterless carriers and foam formulations, which have a good or special skin feeling and which provide many of the desirable attributes of water based emulsions and foams, such as pleasant feeling, absence of stickiness, good spreadability, relatively quick absorption, absence of shine and reduced oily sensation.

Foamable carriers containing only an oil and a surfactant to produce waterless are investigated and developed herein as pharmaceutical and cosmetic waterless carriers suitable for delivery of a wide range of active agents and a wide range of therapeutic and cosmetic effects. In particular, such carriers are substantially a single phase and, in some embodiments, are substantially free of particles. Moreover such carriers are ideal for oil soluble active agents and can nevertheless carry as a homogenous suspension substantial amounts of oil insoluble active agents.

Thus, in several cases, there are provided carriers and compositions for drugs that are more soluble or more stable in hydrophobic solvents; and moreover, simple and elegant formulations to accommodate and stabilize active ingredients in a hydrophobic waterless or substantially waterless environment are provided. The achievement to form a pharmaceutical grade foam with a simple, elegant oil-based composition was unexpected.

Particularly, there are provided improved, easy to use, stable and non-irritating foam formulations, with unique therapeutic or beneficial properties containing a stable or stabilized active pharmaceutical or cosmetic agent.

In one spect, a waterless foamable pharmaceutical composition is described, including a foamable carrier and at least one liquefied or compressed gas propellant wherein the foamable carrier consists essentially of:
> about 60% to about 98% by weight of at least one liquid oil; and
> about 2% to about 40% by weight of a surfactant, wherein the surfactant includes at least a glyceride;

wherein the foamable carrier is substantially a single phase and wherein upon dispensing the foamable carrier composition forms a breakable foam that is thermally stable, yet breaks easily upon application of sheer force.

In some embodiments, the carrier is a single phase.

In some embodiments, the glyceride is a monoglyceride, diglyceride, or a triglyceride.

In some embodiments, the side chain of the monoglyceride, diglyceride, or triglyceride is a C8-C24 saturated hydrocarbon.

In some embodiments, the side chain of the monoglyceride is a C8-C24 saturated hydrocarbon and the side chain of the diglyceride or triglyceride is a C8-C14 saturated hydrocarbon.

In some embodiments, the surfactant further comprises a surfactant selected from the group consisting of polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59, a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, isoceteth-20 and mono-, and di- and tri-esters of sucrose with fatty acids.

In some embodiments, the side chain of the monoglyceride contains at least 8 carbon atoms.

In some embodiments, the monoglyceride is glyceryl monostearate.

In some embodiments, the monoglyceride is a solid.

In some embodiments, at least one liquid oil includes mineral oil.

In some embodiments, at least one oil is mineral oil, MCT oil, liquid paraffin, vegetable oil, essential oil, organic oil, lipid, or a mixture thereof.

In some embodiments, the oil is a mixture of light mineral oil and heavy mineral oil.

In some embodiments, the weight ratio of the light mineral oil to the heavy mineral oil ranges from about 1:1 to about 1:2.

In some embodiments, the waterless foamable pharmaceutical composition further inclues an active agent.

In some embodiments, the active agent is soluble in the liquid oil, the monoglyceride or the carrier.

In some embodiments, the foamable carrier including the active agent is a substantially homogenous suspension.

In some embodiments, the active agent is selected from the group consisting of an acaricides, an active herbal extract, an age spot and keratose removing agent, an allergen, an alpha hydroxyl acid, an analgesic agent, an androgen, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an anti-hyperkeratosis agent, an anti-infective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an anti-yeast agent, an astringent, a beta-hydroxy acid, benzoyl peroxide, a cardiovascular agent, a chemotherapeutic agent, a corticosteroid, an immunogenic substance, a dicarboxylic acid, a disinfectant, an estrogen, a fungicide, a hair growth regulator, a haptene, a hormone, a hydroxy acid, an immunosuppressant, an immunoregulating agent, an immunomodulator, an immunostimulant, an insecticide, an insect repellent, a keratolytic agent, a lactam, a local anesthetic agent, a lubricating agent, a masking agent, a metal, a metal oxide, a mitocide, a neuropeptide, a non-steroidal anti-inflammatory agent, an oxidizing agent, a pediculicide, a peptide, a pesticide, a progesterone, a protein, a photodynamic therapy agent, a radical scavenger, a refatting agent, a retinoid, a sadative agent, a scabicide, a self tanning agent, a skin protective agent, a skin whitening agent, a steroid, a steroid hormone, a vasoavtive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover and mixtures thereof.

In some embodiments, the active agent is a tetracycline antibiotic agent.

In some embodiments, the tetracycline antibiotic agent includes minocycline or doxycycline.

In some embodiments, the active agent is selected from the group consisting of acyclovir, azaleic acid, clindamycin phosphate, pimicrolimus, Diclofenac potassium; Calcipotriol, Calcitriol, vitamin A acetate, Betamethasone 17-valerate, alpha tocopherol, Imiquimod, Ciclopiroxolamine, and mixtures thereof.

In some embodiments, the composition further includes one or more additional components selected from the group consisting of anti perspirants, anti-static agents, buffering agents, anti-oxidants/free radical scavengers, bulking agents, chelating agents, cleansers, colorants, conditioners, deodorants, diluents, dyes, fragrances, hair conditioners, humectants, modulating agents, pearlescent aids, perfuming agents, permeation enhancers, pH-adjusting agents, occlusive agents, preservatives, protectants, skin penetration enhancers, softeners, solubilizers, sunscreens, sun blocking agents, sunless tanning agents, viscosity modifiers, and vitamins.

In another aspect, a waterless foamable pharmaceutical composition is described, including a foamable carrier and at least one liquefied or compressed gas propellant wherein the foamable carrier comprises:
> about 60% to about 98% by weight of at least one liquid oil;
> about 2% to about 40% by weight of a surfactant, wherein the surfactant includes at least a glyceride; and
> an additive selected from the group consisting of a foam adjuvant and a polymer stabilizer;

wherein the foamable carrier is substantially a single phase and wherein upon dispensing the foamable carrier composition forms a breakable foam that is thermally stable, yet breaks easily upon application of sheer force.

In some embodiments, the carrier is a single phase.

In some embodiments, the glyceride is a monoglyceride, diglyceride, or a triglyceride.

In some embodiments, the side chain of the monoglyceride, diglyceride, or triglyceride is a C8-C24 saturated hydrocarbon.

In some embodiments, the side chain of the monoglyceride is a C8-C24 saturated hydrocarbon and the side chain of the diglyceride or triglyceride is a C8-C14 saturated hydrocarbon.

In some embodiments, the surfactant further comprises a surfactant selected from the group consisting of polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59, a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, isoceteth-20 and mono-, di- and tri-esters of sucrose with fatty acids.

In some embodiments, the foam adjuvant is selected from the group consisting of a fatty alcohol, a fatty acid and a hydroxyl fatty acid.

In some embodiments, a method of delivering an active agent to a patient in need of treatment is described, including administering the waterless foamable pharmaceutical composition including an active agent to a skin surface, a mucosal surface, or a body cavity.

In some embodiments, a method for treating skin or a mucosal surface is described, including administering to the skin or mucosal surface a pharmaceutically effective amount of the waterless foamable pharmaceutical composition including an active agent.

In some embodiments, a method for treating, ameliorating or preventing a disorder is described, including administering to a target site a pharmaceutically effective amount of the waterless foamable pharmaceutical composition including an active agent.

In some embodiments, the pharmaceutical composition includes a combination of at least two active agents.

In some embodiments, the target site is selected from the group consisting of the skin, a body cavity, a mucosal surface, the nose, the mouth, the eye, the ear canal, the respiratory system, the vagina and the rectum.

In some embodiments, the resultant foam of the waterless foamable pharmaceutical composition displays all of the following characteristics:
  a. at least of good quality;
  b. does not collapse immediately upon release;
  c. is breakable on mechanical shear;
  d. has a density below about 0.2 g/mL; and
  e. has a collapse time in excess of about 180 seconds.

In yet another aspect, a method for preparing a substantially single phase, waterless foamable carrier is described, including the steps of:
  (a) preparing a foamable carrier by
    (i) combining about 60% to about 98% by weight of at least one liquid oil with about 2% to about 15% by weight of a monoglyceride at a temperature of at least about 50° C.; and
    (ii) rapidly cooling the combination of one liquid oil and at least one foam stabilizing agent to less than 40° C.; and
  (b) combining the foamable carrier with a compressed gas propellant in a weight ratio of 100:3 to 100:35.

In some embodiments, the cooling step is carried out by placing the foamable carrier in an ice bath.

In some embodiments, foamable carrier is cooled at a rate of at least about 5 degrees/minute.

In some embodiments, the foamable carrier is cooled to a temperature of at least about 25° C.

In some embodiments, the fatty acid side chain of the monoglyceride is saturated.

In some embodiments, the monoglyceride is glyceryl monostearate.

In some embodiments, a foamable composition as described in any of the embodiments for use in therapy is described.

In some embodiments, a foamable composition as described in any of the embodiments for treating a disorder selected from the group consisting of skin, body cavity, mucosal membrane, ear channel, eye, nasal, oral, respiratory, vaginal, rectal and urethra disorders, or for treating a disorder selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epi-dermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum, bacterial infection, a fungal infection, a yeast infection, a viral infection and a parasitic infection, wound, ulcer and burn, any disorder that responds to treatment with a hormone, post-surgical adhesions, acne, and rosacea, is described.

In some embodiments, the use of the composition as described in any of the embodiments in the maufacture of a medicament for treating a disorder selected from the group consisting of skin, body cavity, mucosal membrane, ear channel, eye, nasal, oral, respiratory, vaginal, rectal and urethra disorders or for treating a disorder selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum, bacterial infection, a fungal infection, a yeast infection, a viral infection and a parasitic infection, wound, ulcer and burn, any disorder that responds to treatment with a hormone, post-surgical adhesions, acne, and rosacea, is described.

In some embodiments, a waterless foamable pharmaceutical carrier or composition as substantially described in the Examples is described.

DETAILED DESCRIPTION

Figure 1A:
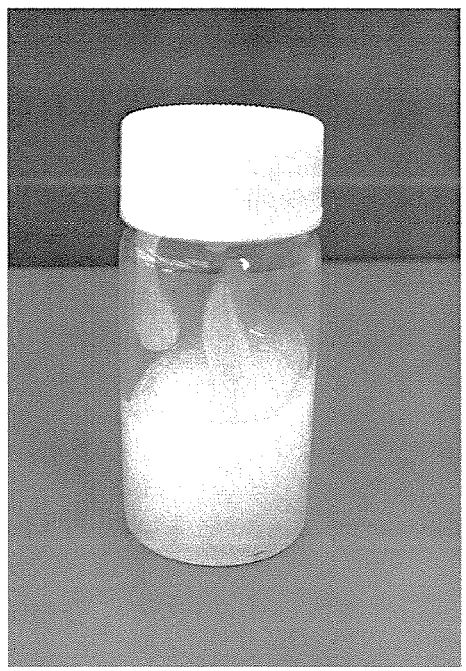
FIGS. 1(a) and 1(b) are photographs of formulation 101 from Example 5 comprising mineral oil and 4% glyceryl monostearate packaged in a glass vial (upright and on side respectively) showing the solidifying effect of glyceride surfactant on liquid oil.

Oil-based, foamable carriers are described herein. The basic foamable carriers are strikingly simple in their composition, as they contain only a liquid oil and a glyceride surfactant. As is generally understood in the art, a glyceride surfactant is an ester formed from glycerol and fatty acids. The fatty acids can react with one, two, or all three of the hydroxyl groups of the glycerol, resulting in mono-, di-, and triglycerides, respectively. When reacting with one or two hydroxyl groups mono or di glyceride surfactants result. When reacting with three hydroxyl groups a triglyceride surfactant can result when at least one of the fatty side chains comprises a hydrophilic group. Otherwise triglycerides are oily substances without customary surfactant properties. Glyceride surfactant compounds are typically non-ionic and can be liquid or solid. As used herein, glyceride surfactants can also include esters of glycerol and other acids such as PEGulated acids, acetylated acids, organic acids.

Surprisingly, when combined with propellant under pressure, these carriers produce high quality, pharmaceutical grade foam. While oil-based foams are known in the art, it is generally understood that these foams are highly unstable. For example, oil-based foams typically drain shortly after dispensing (e.g., 20-30 seconds following dispensing), leading to subsequent collapse of the foam. Accordingly, oil-based foams are considered to lack stability and are not considered suitable for many uses, including as pharmaceutical carriers for topical administration. In contrast, the oil-based foamable carriers described herein generate foams that exhibit excellent stability, as demonstrated by prolonged time to collapse (e.g., greater than about 180 seconds). For example, the foam generated from the carriers described herein is at least short term stable and can be resilient to collapse for at least 2-3 minutes and frequently for 5 minutes after dispensing, at 36° C.

Moreover, the oil-based foamable carriers described herein are single phase carriers. It is conventionally understood in the art that good quality foams require the use of an emulsion. Exemplary emulsions typically used to produce foams include oil-in-water and water-in-oil emulsions. The foamable carriers described herein, however, are single-phase carriers, exhibiting minimal or no partitioning between phases. As a result, the foamable carriers, as well as the resulting foams, are substantially uniform. Thus, active agents are suspended or dissolved uniformly in the foams produced from the carriers, and there is no concern that the active agent is concentrated in a particular phase.

In one or more embodiments, the combination of mineral oil and glyceryl monostearate as the only ingredients in the pre-foam formulation provide a high quality foam. Preparing the foamable composition using both slow and rapid cooling procedures resulted in high quality foam. As used herein 'pre-foam formulation' or "PFF" include ingredients of the pharmaceutical carrier without the compressed or liquefied gas propellant.

In certain embodiments the concentration of the surfactant (including glyceride) and the oil and optional ingredients such as modulating agents, thickeners, fragrances and the like, if present, are selected so that the composition, after filling into aerosol canisters, is flowable, and can be shaken in the canister. In one or more embodiments, the concentrations of the surfactant and the oil are selected such that the viscosity of the composition, prior to filling of the composition into aerosol canisters, is less than 13,000 CPs, and more preferably, less than 10,000 CPs, preferably below about 9000, more preferably below about 6000 cps. In one or more embodiments the concentrations of the surfactant and the oil and optional ingredients, if present, should is selected so that the composition produces a foam of quality preferably at least about of good quality. In one or more embodiments, the composition includes a mixture of oils and, for example the mixture of oils includes silicone. In one or more embodiments, the surfactant (including glyceride), first oil and silicone and optional ingredients, if present, are selected such that the average bubble size should be below about 200 microns, preferably below 150 and more preferably below 100 microns. In one or more embodiments, the concentration of the surfactant (including glyceride), the first oil and the silicone are selected such that the foam density is below about 0.2 g/ml and preferably below about 0.1 g/ml or in the range of about 0.07 g/ml to about 1.5 g/ml. In one or more embodiments, the concentration of the surfactant (including glyceride), the first oil and the silicone are selected such that the foam hardness in the range of about 5 to about 35 grams. In one or more embodiments the foam is of at least about good quality, the bubble size is below 150 microns and the density is between 0.07 and 1.5.

In certain embodiments the oil is mineral oil. In one or more embodiments the mineral oil is a mixture of mineral oils. In certain embodiments the mixture is a mixture of light and heavy mineral oils. In one or more embodiments the ratio of heavy to light mineral oil is from about 1:5; about 2:5, about; 5:11; about 1:2; about: 4:7; about 3:5; about 2:3; about 3:4; about; 5:6; about 1:1; about 6:5; about 4:3; about 3:2; about 5:3; about 7:4; about 2:1; about 11:5; about 5:2; about 5:1; about 10:1; about 15:1; about 20:1 and about 25:1 and any ratio between any of the aforesaid ratios. In one or more embodiments the ratio range of heavy to light mineral oil is from about 1:5 to about 25:1; and preferably in the range of about 2:5 to about 5:1.

The surface active agent (including glyceride) is situated at the gas/liquid interface of the foam, lowering the surface tension at the interface between the gas bubbles and the surrounding oil phase. This property is beneficial for foam formation and also for the prevention of bubble coalescence, thus further stabilizing the foam. In some embodiments, the surface active agent is glyceryl monostearate.

In one or more embodiments there is provided a substantially waterless foamable carrier suitable for use as a vehicle for an active agent, comprising a foamable carrier and at least one liquefied or compressed gas propellant wherein the foamable carrier contains only:

about 60% to about 95% by weight of at least one liquid oil; and least one glyceride that acts as a foam stabilizing agent;
wherein the foamable composition is substantially a single phase, in which an active agent is capable of being dissolved or suspended substantially uniformly; and
wherein the ratio of the foamable carrier to the propellant is 100:03 to 100:35.

In another aspect, as described above, a waterless, single phase foamable carrier containing only one or more liquid oils and a monoglyceride having a saturated fatty acid side chain is provided. In other certain embodiments the side chain can be unsaturated. The ability to form a pharmaceutical quality foam using only these two ingredients is surprising, as it is expected that other components are necessary to stabilize the foam or to promote foam production (e.g., foam adjuvants or polymer stabilizers). Accordingly, in one embodiment, the foamable carrier does not include typical foam stabilizing or foam promoting agents, such as foam adjuvants or polymer stabilizers. The liquid oil is present in the carrier at a concentration of at least about 60% by weight, 70% by weight, 80% by weight, 90% by weight, or 95% by weight. In some embodiments, the liquid oil is present in the carrier at about 60% to about 95% by weight, about 70% to about 95% by weight, about 80% to about 95% by weight, or about 90% to about 95% by weight. The monoglyceride is present in the carrier at less than about, 5% by weight, about 6% by weight, about 7% by weight, about 8% by weight, about 9% by weight, about 10% by weight, or about 15% by weight. In some embodiments, the monoglyceride is present in the carrier at about 5% to about 15% by weight, about 5% to about 10% by weight, about 2% to about 9% by weight, or about 3% to about 8% by weight. In one embodiment, the foamable carrier includes about 1% to about 10% by weight monoglyceride and about 90% to about 99% by weight liquid oil. Exemplary liquid oils include, without limitation light mineral oil and heavy mineral oil. In one embodiment, the liquid oil is heavy mineral oil. In one embodiment, the monoglyceride is glyceryl monostearate. In one embodiment, the foamable carrier includes only heavy mineral oil and glyceryl monostearate.

A method of making the foamable, single-phase, oil-based carriers described herein is further provided. As described herein, the carriers are generally prepared by first combining the liquid oil with the surface active agent (including glyderide) at an elevated temperature, followed by cooling to room temperature. In one embodiment, the components are combined at a temperature of at least about 50° C., at least about 55° C., at least about 60° C. or at least about 65° C. In another embodiment, the components are combined at a temperature between about 50° C. to about 65° C. and preferably between about 60° C. to about 65° C.

In one embodiment, the oil/surface active agent combination is cooled rapidly, by exposing the combination to cold temperatures, e.g., less than about 40° C., less than about 30° C., less than 25° C., or less than about 20° C., or less than about 15° C., or less than about 10° C., or less than about 5° C., or less than about 0° C. or less than about minus 5° C. until it reaches the desired temperature. In one embodiment, rapid cooling is effectuated by placing the combination in an ice bath until it reaches the desired temperature. In another embodiment it is placed in an alcohol water bath. In another embodiment it is placed in a water bath. In a preferred embodiment the cold water bath is below about 20° C. In one embodiment the ice bath is below about 4° C. In a preferred embodiment the alcohol water bath is below about minus 5° C. Without wishing to be bound by a particular theory it is thought that rapid cooling helps to stabilize the formulation by "locking" the hydrophobic ingredients together and stabilizing the oil surfactant structure. The rate of cooling for the rapid cooling procedure ranges from about 2 degrees/minute to about 15 degrees/minute, from about 4 degrees/minute to about 15 degrees/minute or 4 degrees/minute to about 8 degrees/minute. In some embodiments, the rate of cooling is greater than about 2 degrees/minute, about 3 degrees/minute, about 4 degrees/minute, about 5 degrees/minute, about 10 degrees/minute, or about 15 degrees/minute. In an alternative embodiment, the oil/surface active agent combination is cooled slowly. In one embodiment, slow cooling is performed by keeping the mixture at room temperature until it reaches the desired temperature.

In another embodiment, the oil/surface active agent combination is cooled slowly. In one embodiment, slow cooling is effectuated by holding the combination at room temperature until it reaches the desired temperature. The rate of cooling for the slow cooling procedure ranges from less than about 5 degrees/minute to less than about 0.4 degrees/minute, from less than about 4 degrees/minute to less than about 1 degrees/minute or from less than 4 degrees/minute to about 2 degrees/minute. In some embodiments, the rate of cooling is less than about 5 degrees/minute, about 4 degrees/minute, about 3 degrees/minute, about 2 degrees/minute, or about 1 degrees/minute.

In some embodiments, formulations prepared by fast cooling result in improved foam quality, smaller bubble size, viscosity, and density.

The hydrophobic formulations herein have a number of useful attributes making them suitable candidates for topical foamable pharmaceutical and cosmetic carriers. They are inherently stable and inert which are clearly desirable characteristics. They are able to condition the skin and in appropriate amounts can form a barrier to skin moisture loss. By appropriate formulation they can act to improve drug delivery to the skin and yet remain resistant to being washed off. Other attributes of hydrophobic formulations described herein include being able to deliver a substantially uniform and stable composition or foam that ameliorates or overcomes the look and feel of a greasy material, especially where that composition is waterless or substantially so; and facilitating that the active ingredients are uniformly present throughout the formulation and also are effectively delivered and additionally effectively delivered without the use of a short chain alcohol in the formulation.

DEFINITIONS

All % values are provided on a weight (w/w) basis.

The term "waterless", as used herein, means that the composition contains no or substantially no, free or unassociated or absorbed water. Similarly, "waterless" or "substantially waterless" carriers contain at most incidental and trace amounts of water.

By the term "single phase" herein it is meant that after addition of propellant to the composition or carrier, the liquid components of the composition or carrier are fully miscible, and the solid components if any, are either dissolved or suspended in the composition. By substantially a single phase is meant that the composition or carrier after addition of propellant is primarily or essentially a single phase as explained above, but may also have present a small amount of material which is capable of forming or may form a separate phase amounting to less than about 5% of the composition or carrier after the addition of propellant, preferably less than about 3%, and more preferably less than about 1%.

The term "unstable active agent" as used herein, means an active agent which is oxidized and/or degraded within less than a day, and in some cases, in less than an hour upon exposure to air, light, skin or water under ambient conditions.

The identification of a "solvent", as used herein, is not intended to characterize the solubilization capabilities of the solvent for any specific active agent or any other component of the foamable composition. Rather, such information is provided to aid in the identification of materials suitable for use as a part in the foamable carriers described herein.

"Substantially alcohol free" or "alcohol free" in the context herein refers to lower or short chain alcohols, having up to 5 carbon atoms in their carbon chain skeleton, such as ethanol, propanol, isopropanol, butanol, iso-butanol, t-butanol and pentanol are considered less desirable solvents or co-solvents due to their skin-irritating effect. Thus, according to some embodiments, the carrier is substantially alcohol-free i.e., free of short chain alcohols. In other embodiments, the pharmaceutical composition or foam is substantially alcohol-free and comprises less than about 5% final concentration of lower alcohols, preferably less than 2%, more preferably less than 1%.

Applications

The pharmaceutical compositions and carriers described herein are suitable for dermal or external application of an unstable active agents, as well as active agents. Typically, unstable agents break down upon exposure to air, water vapor or upon contact with the skin. The hydrophobic, oil-based carriers described herein provide stable formulations of unstable agents, which are active in situ and, are stable over a time period of at least 1-5 minutes after application. In other embodiments the pharmaceutical compositions and carriers described herein are suitable for mucosal or internal application of an unstable active agents, as well as active agents. The compositions and carriers are substantially non-aqueous, and provide not only a soothing effect to the skin or mucosa, but also provide a therapeutic local and/or systemic effect from the active agent.

In one or more embodiments the carrier is used as the vehicle for delivering a pharmaceutical or cosmetic active agent. In certain embodiments, the active agent is unstable in the presence of water, and in such cases the presence of water in the carrier is clearly not desirable.

The active agent may be insoluble or fully or partially soluble in the carrier and to the extent it is insoluble it may be provided in a substantially homogenous insoluble suspension.

At least one liquid oil may be selected from a mineral oil, a vegetable oil, a medium chain triglycerides (MCT) oil, an essential oil, a therapeutic oil, an organic oil, a hydrogenated castor oil and lipids and mixtures thereof.

The liquid oil may further contain an emollient or a hydrophobic solvent. In some embodiments the liquid oil may contain a solid or semi solid hydrophobic matter, such as a wax, a fatty alcohol, a fatty acid, a hydrogenated oil, an oil which is solid or semi solid at room temperature. An example of a semi solid paste like oil is coconut oil. In a specific embodiment the liquid oil may contain a wax. In another specific embodiments the liquid oil may contain a hydrogenated oil such as hydrogenated caster oil, which is a solid at room temperature. In an embodiment the wax may be a mixture of waxes or comprise beeswax In an embodiment there is provided a waterless foamable carrier, wherein said at least one liquid oil is a mineral oil.

In an embodiment there is provided a waterless foamable carrier, wherein the oil is selected from mineral oil, hydrogenated castor oil and MCT oil.

In one or more embodiments the liquid oil is substantially free of particles. In a preferred embodiment the liquid oil is free of particles as determined by normal microscopic examination. In other words the foamable carrier prior to addition of active agent is substantially a single phase, and preferably a single phase. In one or more embodiments the foamable composition after addition of active agent is substantially a single phase, preferably a single phase. In yet other embodiments the foamable composition after addition of active agent is substantially a homogenous suspension of active agent.

In some embodiments, the foamable carrier has the following property: a foam quality of at least good up to excellent; and at least one other property selected from: specific gravity in the range of about 0.05 gr/mL to about 0.20 gr/mL; a foam texture of a very fine creamy foam consistency to a fine bubble structure consistency; a sustainability of more than 95% for at least one minute upon release thereof to a surface from an aerosol can; capable of withstanding at least one freeze thaw cycle without substantial change; having a mean bubble size of less than about 200 micron; and compatibility with at least one active agent.

In some cases, the foamable carrier has at least four of the properties. In some other cases, the carrier has all of the properties.

The target site for the compositions incorporating the foamable carrier includes the skin, a body cavity, a mucosal surface, the nose, the mouth, the eye, the ear canal, the respiratory system, the vagina, the urethra and the rectum.

In one or more embodiment, the foam formulations including an liquid oil are used with a tetracycline antibiotic such as doxycycline or minocycline for example for the treatment of a microbial infection or to treat acne. The use of an oil-based foam formulation for the treatment of acne runs counter to conventional approach, which avoid oily bases as exacerbating the underlying acne condition. In contrast, the current formulations moisturize and protect the skin. Initial investigations indicate that waterless hydrophobic foam preparations have a good "skin feel," are quickly absorbed and are not tacky.

The present invention relates to a foamable carrier suitable for external administration of an unstable, particularly water unstable, active agent. In other embodiments relates to its internal administration.

Liquid Oil

Exemplary liquid oils include, without limitation, one or more of a mineral oil, vegetable oil, MCT oil (i.e., medium chain triglycerides, in which the fatty side chains can include caproic (C6), caprylic (C8), capric (C10) and lauric acid (C12)), an essential oil, a therapeutic oil, an organic oil or a lipid. In some embodiments, the liquid oil is a mineral oil. The mineral oil may be heavy or light or a combination thereof. MCT oil may be obtained as a mixture of capric/caprylic triglycerides. In some embodiments, the liquid oil consists essentially of a mineral oil. In another embodiment it may comprise a majority of mineral oil combined with one or more other oils. In one or more embodiments the liquid oil may further comprise an emollient. In one or more embodiments the liquid oil may further comprise a hydrophobic solvent. In one or more embodiments the liquid oil may further comprise a polypropylene glycol (PPG) alkyl ether such as a PPG stearyl ether for example PPG-15. In some embodiments, the liquid oil consists of an essential oil or a therapeutic oil. In other embodiments the liquid oil is combined with an emollient.

In some embodiments, the liquid oil is one or more of mineral oil, MCT oil, liquid paraffin, vegetable oil, essential oil, therapeutic oil, organic oil, and lipid.

An essential oil is a concentrated, hydrophobic liquid containing volatile aroma compounds from plants usually conveying characteristic fragrances. Non limiting examples include lavender, peppermint, and eucalyptus. A therapeutic oil is a hydrophobic liquid which is said to have a therapeutic effect or to have associated with it certain healing properties. Therapeutic oils contain active biologically occurring molecules and, upon topical application, exert a therapeutic effect. Non limiting examples include Manuka oil, rosehip oil, which contains retinoids and is known to reduce acne and post-acne scars, and tea tree oil, which possesses anti-microbial activity including antibacterial, antifungal and antiviral properties as well as any other therapeutically beneficial oil known in the art of herbal medication. Many essential oils, are considered "therapeutic oils." Other non limiting examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla, verbena.

Surface-Active Agents

The carriers described herein contain a glyceride surface-active agent (also termed "surfactants"). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants can be significant in producing breakable forms of good quality. Surfactants can play a significant role in foam formation where the foamable formulation is a single phase composition.

In selecting a suitable surfactant or surfactant combination for use in the substantially single phase carriers described herein selection relates to a multiple of factors including but not limited to solubility and miscibility in the liquid oil to produce substantially a single phase; the ability to form foam of quality; the ability to stabilize the extruded foam; a HLB value which preferably suggests potential compatibility with the liquid oil; and solubility of surfactant in the formulation. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). For oil based waterless systems HLB values may have little significance other than to indicate the proportion of an amphiphilic molecule that is hydrophobic and therefore potentially more at home in an oil single phase environment.

In certain embodiments the glyceride surfactant can have thickening properties. In certain embodiments the glyceride surfactant can affect the viscosity of the pre foam formulation (PFF). In certain other embodiments the glyceride surfactant has little or no effect. In certain embodiments the glyceride surfactant can induce the oil based formulation to gel. The concentration of the glyceride surfactant agent in combination with the oil, e.g., a mixture of a first oil and silicone, and optional ingredients, if present, is selected so that the composition, after filling into aerosol canisters, is flowable, and can be shaken in the canister. In one or more embodiments, the concentration of the surfactant agent is selected such that the viscosity of the composition, prior to filling of the composition into aerosol canisters, is less than 13,000 CPs, and more preferably, less than 10,000 CPs, preferably below about 9000, more preferably below about 6000 cps; In one or more embodiments average bubble size of the resultant foam should be below about 200 microns, preferably below 150 and more preferably below 100 microns. In one or more embodiments foam density is below about 0.2 preferably below about 0.1 g/ml. In one or more embodiments hardness of the resultant foam is in the range of about 5 to about 35.

Exemplary glyceride surface active agents include, without limitation, stearic acid derived esters of glycerol. In other embodiments the surfactant is monoglyceride, diglyceride, or triglyceride, wherein the side chain of the monoglyceride, diglyceride, or triglyceride is a C8-C24 hydrocarbon. In some embodiments, the fatty acid side chain of the glyceride is saturated. One nonlimiting example of a monoglyceride is glyceryl monostearate, which has an HLB of approximately 4. In still other embodiments the surfactant is glycerol palmitostearate, In other embodiments, other surfactants such as PEG 40 Stearate (Myrj 52), PEG 100 Stearate (Myrj 59), PEG 40 stearate, or a mixture of one or more of these compounds may also be present.

According to one or more embodiments the composition contains a single glyceride surface active agent having an HLB value between about 2 and 9, or more than one surface active agent at least one of which is a glyceride surface active agent and the weighted average of their HLB values is between about 2 and about 9.

According to one or more embodiments the composition contains a single glyceride surface active agent having an HLB value between about 7 and 14, (preferably about 7 to about 12) or more than one surface active agent at least one of which is a glyceride surface active agent and the weighted average of their HLB values is between about 7 and about 14 (preferably about 7 to about 12).

According to one or more other embodiments the composition contains a single glyceride surface active agent having an HLB value between about 9 and about 19, or more than one surface active agent at least one of which is a glyceride surface active agent and the weighted average of their HLB values is between about 9 and about 19.

In a waterless or substantially waterless environment a wide range of HLB values may be suitable. In one or more embodiments the HLB may not play a role in a single phase system The glyceride is usually a non-ionic surfactant. It can also be ionic such as phosphatidyl choline. In a preferred embodiment the glyceride surfactant is non-ionic. In one or more embodiments, the non-ionic surface active agent is a stearic acid derived ester of glycol. In other embodiments the surfactant is monoglyceride, diglyceride, or triglyceride, including wherein the side chain of the monoglyceride, diglyceride, or triglyceride is a C8-C24 hydrocarbon, such as a fatty acid ester of glycerol mono, di, or tri fatty ester of stearic acid, or a mono, di or tri fatty ester of palmitic acid, A preferred gyceride is glyceryl monostearate.

In one or more embodiments the surfactant is selected to produce a foam of quality being of least of about good quality foam and preferably of excellent quality foam. In one or more embodiments the surfactant includes, a fatty acid ester of glycerol, such as a mono, di or tri fatty ester of stearic acid or palmitic acid or arachidic acid or beheneic acid such as, those listed below (Table 1).

TABLE 1

Glycerol fatty acid esters

| Ester | Function | Solubility | Fatty acid (main) |
|---|---|---|---|
| Glyceryl Behenate | Thickener, lubricant | Practically insoluble in oil and water | Beheneic (C22) |
| Glyceryl monooleate | Non ionic Surfactant | Soluble in oil and practically insoluble in water | Oleic (double bond in side chain (C18) |
| Glyceryl monostearate (GMS) | Non ionic emulsifying agent | Soluble in mineral oil and practically insoluble in water | Stearic (C18) |
| Glyceryl Palmitostearate | Sustained release, lubricant | Practically insoluble in mineral oil and water | Mixture of mono (~<17%), di, and triglycerides of C16 and C18 fatty acids |

In one or more embodiments the glyceride surfactant is used on its own with the oil. In certain other embodiments the glyceride surfactant is used in combination with one or more other surfactants. In an embodiment the combination is, for example, glyceryl monostearate and PEG 100 stearate. Other similar combinations are readily envisaged.

In certain embodiments, surfactants are selected which can provide a close packed surfactant layer. To achieve such objectives combinations of at least two surfactants are selected. Preferably, they should be complex emulgators and more preferably they should both be of a similar molecular type; for example, a pair of esters, for example, PEG-40 stearate and polysorbate 80.

In one or more embodiments, the carrier may further include an additional non-ionic surfactant. Non limiting examples of non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, isoceteth-20 and mono-, di- and tri-esters of sucrose with fatty acids. In certain embodiments, suitable sucrose esters include those having high monoester content, which have higher HLB values. However, sorbitan esters are not used alone as primary surfactants. In an embodiment if present sorbitan esters are used in combination with one or more primary surfactants and functions as a secondary or co-surfactant. In some embodiments one or more of these other non ionic surfactants may be used in combination with a stearic acid derived ester or with a monoglyceride, diglyceride, or triglyceride surfactant.

Non-limiting example of non-ionic surfactants that have HLB of about 7 to about 12 is glyceryl monostearate/PEG 100 stearate (Av HLB~11.2).

Non-limiting examples of surfactants, which have a HLB of 4-19 are set out in the Table below:

| Surfactant | HLB |
|---|---|
| glyceryl monostearate/PEG 100 stearate | Av ~11.2 |
| Glyceryl monostearate | ~4 |
| peg 40 stearate | ~16.9 |
| polysorbate 80 | ~15 |
| sorbitan stearate | ~4.7 |
| Sorbitan monooleate (span 80) | ~4.3 |
| ceteareth 20 | ~15.7 |
| steareth 20 | ~15.3 |
| ceteth 20 | ~15.7 |
| ceteth 2 (Lipocol C-2) | ~5.3 |
| PEG-30 Dipolyhydroxystearate | ~5.5 |
| sucrose distearate (Sisterna SP30) | ~6 |
| polyoxyethylene (100) stearate | ~18.8 |

More exemplary stabilizing surfactants which may be suitable for use in the present invention are found below.

PEG-Fatty Acid Monoester Surfactants, such as:

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants, such as:

| Chemical name | Product example name | HLB |
|---|---|---|
| PEG-4 dilaurate | Mapeg ™ 200 DL (PPG), Kessco ™ PEG 200 DL (Stepan), LIPOPEG 2-DL (Lipo Chem.) | 7 |
| PEG-4 distearate | Kessco ™ 200 DS (Stepan. sub) | 5 |
| PEG-32 dioleate | Kessco ™ PEG 1540 DO (Stepan) | 15 |
| PEG-400 dioleate | Cithrol 4DO series (Croda) | >10 |
| PEG-400 distearate | Cithrol 4DS series (Croda) | >10 |
| PEG-20 glyceryl monooleate | Tagat ™ O (Goldschmidt) | >10 |

Transesterification Products of Oils and Alcohols, such as:

| Chemical name | Product example name | HLB |
| --- | --- | --- |
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
| --- | --- | --- |
| Polyglyceryl-6 dioleate | Caprol ™ 6G20 (ABITEC); PGO-62 (Calgene), PLUROL OLEIQUE CC 497 (Gattefosse)Hodag | 8.5 |

PEG-Sorbitan Fatty Acid Esters, such as:

| Chemical name | Product example name | HLB |
| --- | --- | --- |
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan monooleate | Tween-80 (Atlas/ICI), Crillet 4 (Croda) | 15 |

Sugar Ester Surfactants, such as:

| Chemical name | Product example name | HLB |
| --- | --- | --- |
| Sucrose distearate | Sisterna SP50, Surfope 1811 | 11 |

In one or more embodiments the surface active agent is a complex emulgator in which the combination of two or more surface active agents can be more effective than a single surfactant and provides a more stable formulation or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

In one or more embodiments, the surface-active agent includes at least one non-ionic surfactant. Ionic surfactants are known to be irritants.

In a preferred embodiment, the surface active agent, the composition contains a non-ionic surfactant. In another preferred embodiment the composition includes a mixture of non-ionic surfactants as the sole surface active agent.

In one or more embodiments, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher HLB values.

For foams in selecting a suitable surfactant or combination thereof it should be borne in mind that the upper amount of surfactant that may be used may be limited by the shakability of the composition. If the surfactant is non-liquid, it can make the formulation to viscous or solid. Subject to its miscibility solid surfactants may be added first, and may require gentle warming and then cooling before being combined with the other ingredients. In general terms, as the amount of non-liquid surfactant is increased the shakability of the formulation reduces until a limitation point is reached where the formulation can become non-shakable and unsuitable. Thus in one embodiment, any effective amount of surfactant may be used provided the formulation remains shakable. In other certain limited embodiments the upper limit for foamable formulations may be determined by flowability such that any effective amount can be used provided the formulation is sufficiently flowable to be able to flow through an actuator valve and be released and still expand to form a good quality foam. This may be due without being bound by any theory to one or more of a number of factors such as the viscosity, the softness, the lack of crystals, the pseudoplastic or semi pseudo plastic nature of the composition and the dissolution of the propellant into the composition.

In certain embodiments the amount of surfactant or combination of surfactants is between about 0.05% to about 20%; between about 0.05% to about 15%, or between about 0.05% to about 10%. In a preferred embodiment the concentration of surface active agent is between about 0.2% and about 8%. In a more preferred embodiments the concentration of surface active agent is between about 1% and about 6% or between about 1% and about 4%.

In an embodiment, the pharmaceutical compositions described herein include one or more additional components that impart various desirable cosmetic or pharmaceutical characteristics to the formula, but are not essential. Such additional components include but are not limited to anti perspirants, anti-static agents, buffering agents, anti-oxidants/free radical scavengers, bulking agents, chelating agents, cleansers, colorants, conditioners, deodorants, diluents, dyes, foam adjuvants, fragrances, hair conditioners, humectants, modulating agents, pearlescent aids, perfuming agents, permeation enhancers, pH-adjusting agents, occlusive agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

In an embodiment, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment, the additional component is a humectant.

In an embodiment no preservative is added since the formulation is a waterless oil base formulation having an Aw (Water Activity) value of less than 0.9, less, or less than about 0.8, or less than about 0.7 or less than about 0.6 and preferably less than about 0.5 which is below the level of microbial proliferation. In certain limited embodiments, the additional component is an oil soluble preservative. Suitable preservatives include but are not limited to C12 to C15 alkyl benzoates, alkyl p-hydroxybenzoates, castor oil, cetyl alcohols, chlorocresol, cocoa butter, coconut oil, diisopropyl adipate, dimethyl polysiloxane, fatty acids, fatty alcohols, hexadecyl alcohol, jojoba oil, lanolin oil, mineral oil, oleic acid, olive oil, polyoxypropylene butyl ether, polyoxypropylene cetyl ether, silicone oils, stearic fatty acid, vitamin E, vitamin E acetate and derivatives, esters, salts and mixtures thereof.

In an embodiment, the additional component is a skin penetration enhancer.

Optionally, the waterless foamable carrier may further include a foam adjuvant selected from the group consisting of a fatty alcohol, a fatty acid and a hydroxyl fatty acid for example to increase the foaming capacity of surfactants and/or to stabilize the foam and or to improve spreadability and absorption of the composition. In one or more embodiments, the fatty alcohols have 14 or more carbons in their carbon chain, such as cetyl alcohol and stearyl alcohol (or mixtures thereof), arachidyl alcohol (C20), behenyl alcohol (C22), 1-triacontanol (C30), as well as alcohols with longer carbon chains (up to C50) or mixtures thereof In one or more embodiments, the fatty acids have 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof Optionally, the carbon atom chain of the fatty alcohol or the fatty acid may be branched and or have at least one double bond The carbon chain of the fatty acid or fatty alcohol also can be substituted with a hydroxyl group, such as 12-hydroxy stearic acid.

In one or more embodiments the modulating agent is used in a waterless composition with surfactant. The term modulating agent is used to describe an agent which can improve the stability of or stabilize a carrier or a foamable composition and/or an active agent by modulating the effect of a substance or residue present in the carrier or composition. The substance or residue may, for example, be acidic or basic or buffer system (or combinations thereof) and potentially alter an artificial pH in a waterless or substantially non-aqueous environment, such a, by acting to modulate the ionic or polar characteristics and any acidity or basesity balance of a waterless or substantially non-aqueous carrier, composition, foamable carrier or foamable composition or resultant foam or it may be a chelating or sequestering or complexing agent or it may be one or more metal ions which may act as a potential catalyst in a waterless or substantially non-aqueous environment or it may be an ionisation agent or it may be an oxidizing agent.

In an embodiment, the modulating or additional component is a pH adjusting agent or a buffering agent and can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the waterless solvent to enable it to "mop up" or "lock" metal ions such as EDTA or other such pharmaceutically or cosmetically acceptable.

Modulating agents may be added to the compositions of the subject invention, preferably from about 0.1% to about 10%, more preferably from about 1% to about 5%, of the composition. Where the active agent itself is the modulating agent alone or in combination with another modulating agent it will be added at an effective dose which may be outside these ranges. For example azaleic acid may be at about 15% of the composition. In an embodiment sufficient modulating agent is added to achieve an artificial pH in which the active agent is preferably stable. Such artificial pH may be acidic, maybe basic or may be neutral Further detail regarding modulating agents is found in co-pending Published U.S. Patent Application 2008/0206159, which is hereby incorporated in its entirety by reference.

The modulating agent to the foamable composition is useful for stabilizing pharmaceutical and cosmetic active agents which are unstable in certain pH conditions. It is known, for example, that active agents, which contain ester bond in their structure tend to undergo hydrolysis of the ester bond at basic pH levels. Therefore, the addition of an agent, which avoids the formation of basic pH condition and thus, prevents degradation of such active agents. Many steroid compounds are known to undergo rearrangement at high pH, and again, adding an acidic modulating agent helps prevent such degradation. Another example of a pH-sensitive active agent is vitamin D, which degrades at low pH levels. In such a case, the addition of a basic modulating agent, such as triethanol amine is useful to maintain acceptable stability of this active agent.

It is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since better protection against vaginal infection is attained in pH lower than 4.

In one or more embodiments, the modulating agent may also be a preservative or an antioxidant or an ionization agent. Any preservative, antioxidant or ionization agents suitable for pharmaceutical or cosmetic application may be used. Non-limiting examples of antioxidants are tocopherol succinate, ascorbic acid (vitamin C) and its salts, propyl galate, butylated hydroxy toluene and butyl hydroxy anisol. Non-limiting examples of positive ionization agents are benzyl conium chloride, and cetyl pyridium chloride. Non-limiting examples of negative ionization agents are sodium lauryl sulphate, sodium lauryl lactylate and phospholipids. In one or more embodiments the modulating agent is a flavonoid for example quercitin and/or rutin.

A safe and effective amount of an anti-oxidant/radical scavenger may be added to the compositions of the subject invention, preferably from about 0.1% to about 10%, more preferably from about 1% to about 5%, of the composition.

Propellants

Examples of suitable propellants include volatile hydrocarbons such as butane, propane, isobutane and fluorocarbon gases, or mixtures thereof.

In an embodiment the propellant is 1681 or is AP 46, which is a mixture of propane, isobutane and butane. In another embodiment it is AP 70, which is a mixture of propane, isobutane and butane with a higher pressure.

The propellant makes up about 3-25 wt % of the foamable composition. In some circumstances the propellant may be up to 35%. Thus, in some embodiments, the ratio of the liquefied or compressed gas propellant to the other components of the formulation ranges from about 3:100 to about 25:100 by weight, from about 3:100 to about 35:100, or from about 3:100 to about 45:100. In some embodiments, the ratio of the liquefied or compressed gas propellant to the other components of the formulation is at least about 3:100, at least about 10:100, at least about 15:100, at least about 20:100, or at least about 25:100. The propellants are used to generate and administer the foamable composition as a foam. The total composition including propellant, foamable carriers and optional ingredients is referred to as the foamable composition.

Alcohol and organic solvents render foams inflammable. Fluorohydrocarbon propellants, other than chloro-fluoro carbons (CMCs), which are non-ozone-depleting propellants, are particularly useful in the production of a non-flammable foamable composition. A test according to European Standard prEN 14851, titled "Aerosol containers—Aerosol foam flammability test" revealed that carriers containing an organic carrier that contains a hydrophobic organic carrier and/or a solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect include propellants made by DuPont under the registered trademark Dymel, such as 1,1,1,2 tetrafluorethane (Dymel 134), and 1,1,1,2,3,3,3 heptafluoropropane (Dymel 227) 1,1, difluoro ethane (Dymel 152) and 1,1,1,3,3,3 hexafluoropropane HFCs possess Ozone Depletion Potential of 0.00 and thus, they are allowed for use as propellant in aerosol products.

In one or more embodiments foamable compositions comprise a combination of a HFC and a hydrocarbon propellant such as n-butane or mixtures of hydrocarbon propellants such as propane, isobutane and butane. Where mixtures are used they can be selected to generate different levels of pressure. For example 1681 has a lower pressure than AP 40 which is lower than that provided by propane alone. The amount and pressure of the propellant is selected to provide foam release without powerful jets and without tailing such that the foam is released in ideally a substantially single unbroken pulse, In one or more embodiments "liquification" occurs following adding the propellant, which in turn will affect the viscosity substantially or radically. Thus in one or more embodiments the oil carriers are liquefied or further liquefied by the propellant.

Composition and Foam Physical Characteristics and Advantages

A pharmaceutical or cosmetic composition manufactured using the foamable carrier is very easy to use. When applied onto the body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition is stable, having an acceptable shelf-life of at least one year, or preferably, at least two years at ambient temperature, as revealed in accelerated stability tests.

The composition should also be free flowing, to allow it to flow through the aperture of the container, e.g., and aerosol container, and create an acceptable foam.

Quantitative and Qualitative Characteristics
Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery;

Grade G (good): rich and creamy in appearance, very small bubble size, "dulls" more rapidly than an excellent foam, retains creaminess upon spreading on the skin, and does not become watery;

Grade FG (fairly good): a moderate amount of creaminess noticeable, bubble structure is noticeable; upon spreading on the skin the product dulls rapidly and becomes somewhat lower in apparent viscosity;

Grade F (fair): very little creaminess noticeable, larger bubble structure than a "fairly good" foam, upon spreading on the skin it becomes thin in appearance and watery;

Grade P (poor): no creaminess noticeable, large bubble structure, and when spread on the skin it becomes very thin and watery in appearance;

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

Foam Physical Characteristics

In terms of foam consistency and texture an acceptable foam is one that exhibits the following characteristics:

Upon release from an aerosol can, a foam mass is created, which is sustained on a surface for at least one minute, more preferably at least two minutes, and yet more preferably for at least 3 minutes or more, say even about 5 minutes.

Foam texture should vary from a very fine creamy foam to a fine bubble structure.

In terms of spreadability and absorption an acceptable foam is one, that does not readily collapse upon dispensing on the skin; spreads easily on a skin surface; at least partially absorbed following rubbing onto the skin, and more preferably, substantially absorbed following rubbing on the skin.

In terms of tactile properties an acceptable foam is one, that: creates a pleasant feeling after application; leaves minimal oily residue; and leaves minimal shiny residual look.

Foam Collapse

A further aspect of the foam is breakability. Quick-break foams, including but not limited to thermally sensitive foams, immediately or rapidly collapse upon exposure to skin temperature and, therefore, cannot be applied on the hand and afterwards delivered to the afflicted area.

The foam has several notable advantages, when compared with hydroalcoholic foam carriers, such as (1) Breakability. The foam is thermally stable and breakable under sheer force but is not "quick breaking" which allows comfortable application and well directed administration to the target area;

(2) Skin drying and skin barrier function. Short chain alcohols are known to dry the skin and impair the integrity of the skin barrier. By contrast, having an liquid oil in the composition protects and improves moisturization and does not cause unwanted skin barrier damage.

Irritability

Due to the lack of lower alcohols (C1-05) and improvement in skin barrier function, the use of non-ionic surfactants, and improvement in skin barrier function, skin irritability is eliminated or minimized.

Another property of the foam is specific gravity, as measured upon release from the aerosol can. Typically, oily foams have specific gravity of less than 0.20 g/mL; or less than 0.15 g/mL; or less than 0.12 g/mL, depending on their composition and on the propellant concentration. Preferably, specific gravity is in the range of about 0.05 gr/mL to about 0.20 gr/mL, more preferably between about 0.07 gr/mL and about 0.15 gr/mL.

Shakability

'Shakability' means that the composition contains some or sufficient flow to allow the composition to be mixed or remixed on shaking. That is, it has fluid or semi fluid properties. In some very limited cases it may still be possible to have a foamable composition which is flowable but not apparently shakable.

Breakability

A breakable foam is thermally stable or substantially so, yet breaks under sheer force. The breakable foam is not "quick breaking", i.e., it does not readily collapse upon exposure to body temperature environment. Sheer-force breakability of the foam is clearly advantageous over thermally induced breakability, (due to, for example, the presence of alcohol) since it allows comfortable application and well directed administration to the target area.

Chemical Instability and Stability

By chemical instability of one or more active agents is meant that at least one of the one or more active agents is susceptible to one or more of inter alia reaction, breakdown, ionization or oxidation or the rate thereof is increased when incorporated into a pharmaceutical or cosmetic carrier that is non aqueous or substantially non aqueous.

Conversely by chemical stability of one or more active agents is meant that at least one of the one or more active agents is less susceptible to one or more of inter alia reaction, breakdown, ionization or oxidation or the rate thereof is impeded when incorporated into a pharmaceutical or cosmetic carrier that is non aqueous or substantially non aqueous.

"Chemically stable" or "chemical stability" may be defined as demonstrating substantially no or minimal breakdown from oxidation 72 hours after mixing with the carrier or agent when stored at about at least 25° C. Substantially no or minimal breakdown may be determined using standard HPLC methods or other methods, where the mass of the compound is determined at time 0 (i.e., within about 1 hour after mixing with the carrier or foamable pharmaceutical composition) and about 72 hours after mixing, and wherein at least about 90% by mass of the compound is detected at about 72 hours compared to time 0. Alternatively, degradation products may be determined using HPLC methods known in the art or other methods, where the mass of the degradation products is determined at time 0 and about 72 hours after mixing, and wherein less than about 1% by mass of the compound in the mixture is degradation products. When the compound is minocycline, a suitable degradation product for purposes of determining "chemical stability" or "chemically stable" is 4-epiminocycline.

Pharmaceutical Composition

The foamable carrier is an ideal vehicle for active pharmaceutical ingredients and/or active cosmetic ingredients. In the context, active pharmaceutical ingredients and active cosmetic ingredients are collectively termed "active agent" or "active agents". The oily waterless formulations optionally coupled with the use of modulating agents can uniquely be adapted to protect and preserve active agents when stored in compatible sealed canisters with propellant A foamable composition, comprising an active agent has the following advantages:

1. The foamable composition provides a preferred solvent for active agents, particularly for poorly soluble or water-insoluble agents;
2. The provision of a single phase foamable composition facilitates a co-solvent effect, resulting increased concentrations of soluble active agent in the dosage form, thus facilitating enhanced skin penetration of the active agent. In many cases, increased penetration is positively correlated with improved clinical outcome. In certain case, attaining an increased drug penetration into the target site of action enables a decrease of treatment frequency, for example, from twice or three times daily to once daily. Oils with a secondary solvent can act as skin penetration enhancers, thus, increasing drug residence time in the target area and increasing clinical efficacy, as detailed above;
3. The fact that the composition contains no or little water minimizes the probability of degradation of water-sensitive active agents. Furthermore, as exemplified herein, a foam containing an oil with no water at all can be formed in accordance with the composition and process. Such carriers ensure high stability of water sensitive active agents;
4. The foamable oil composition is contained in an impermeable pressurized packaging presentation is impermeable and thus, the active agent is not exposed to environmental degradation factors, such as light and oxidizing agent during storage.

Thus, in one or more embodiments, the pharmaceutical composition includes at least one therapeutic agent, in a therapeutically effective concentration. Therapeutic agents are described herein. In addition, compounds disclosed in International Patent Publication No. WO 2004/03284, which is incorporated by reference in its entirety are suitable for use in the pharmaceutical carriers described herein.

In an embodiment the therapeutic agent is soluble in the foamable composition. In alternative embodiments the therapeutic agent is partially soluble and in further embodiments the therapeutic agent is insoluble in the formulation. Where the agent is insoluble or partially soluble it is provided as a homogenous suspension. In certain embodiments the homogeneous suspension remains homogenous over a substantial period of time suitable for pharmaceutical use. In other embodiments the agent may crystallize, precipitate or separate out but homogeneity is fully reversible on shaking.

Oil soluble active agents may be readily used in the oil/silicone surfactant compositions described herein. A short list of non limiting examples of oil soluble active agents include calcipotriol, calcitriol, ciclopirox olamine, benzocaine. Other examples are terbinofine, diclofenac, tacrolimus and pimecrolimus and also oil soluble vitamins. Estradiol, progesterone are non limiting examples of sparingly oil soluble agents.

Because the foamable carriers described herein can provide a substantially waterless, high oil content environment, particular classes of active pharmaceutical ingredients (APIs) will benefit from their inclusion in the composition. For example, active agents that are water sensitive, such as minocycline, doxycycline and other tetracycline drugs, vitamin D (e.g., calcipotriol and calcitriol), can have improved stability in the waterless composition. API's that are esters or amides are generally prone to hydrolysis by water and would benefit from a water free oil environment. API's that are sensitive to free radical attack or oxidation also would benefit from a water free oil environment. Similarly, active agents that are sensitive to specific pH level (which prevails in the presence of water) will also benefit. Exemplary APIs that would benefit from the waterless carriers according to one or more embodiments include Vitamin D analogs and derivatives that degrade at low pH and corticosteroids that degrade at high pH. Oil soluble drugs can also be included in the carriers, such as corticosteroids, immunomodulators, such as tacrolimus ad pimecrolimus, oil-soluble vitamins, e.g., vitamin A and derivatives thereof, other retinoids, vitamin E. Certain APIs may possess more than one of the above features, and thereby benefit even further from the waterless carriers.

In one or more embodiments, non limiting examples of at least one therapeutic agent include a steroidal antiinflammatory agent, a nonsteroidal anti-inflammatory drug, an immunosuppressive agent, an immunomodulator, an immunoregulating agent, a hormonal agent, an antibiotic agent, an antifungal agent, an antiviral agent, an antiparasitic agent, a vasoactive agent, a vasoconstrictor, a vasodilator, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an anti-allergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, an antibiotic agent, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

In an embodiment, the active agent is an active herbal extract. Suitable active herbal extracts include but are not limited oil extracts such as tea tree oil.

Several disorders of the skin, body cavity or mucosal surface (e.g., the mucosa or the cavity of the nose, mouth, eye, ear, vagina or rectum) involve a combination of etiological factors. For example, fungal and bacterial infections and that are inflamed and have symptoms of redness and/or itching warrant therapy that combines an anti-infective agent and an anti-inflammatory agent. Thus, in several cases, combining at least two active agents that treat different etiological factors results in a synergistic effect and consequently higher success rate of the treatment.

In certain cases, the composition contains two active agents, where each of the active agents require a different pH environment in order to remain stable. For example, corticosteroids are typically stable at acidic pH values (they have a maximum stability at a pH of about 4-6) and of vitamin D analogues are typically stable at basic pH values (they have a maximum stability at pH values above about 8). In order to circumvent the problem of instability it is desirable that the composition is substantially water-free. The term "substantially water-free" is intended to indicate that the composition has a water content below about 5%, preferably below about 2%, such as below about 1.5%. Preferably the composition is water-free.

Microsponges

Microsponges (or microspheres) are rigid, porous and spongelike round microscopic particles of cross-linked polymer beads (e.g., polystyrene or copolymers thereof), each defining a substantially noncollapsible pore network. Microsponges can be loaded with an active ingredient and can provide a controlled time release of the active ingredient to skin or to a mucosal membrane upon application of the formulation. The slow release is intended to reduce irritation by the active. Microsponge® delivery technology was developed by Advanced Polymer Systems. In one or more embodiments the composition comprises one or more active agents loaded into Microponges with a waterless carrier described herein, which may also comprise a modulating agent.

Fields of Applications

The pharmaceutical compositions described herein are suitable for treating any infected surface. In one or more embodiments, pharmaceutical compositions are suitable for administration to the skin, a body surface, a body cavity or mucosal surface, e.g., the cavity and/or the mucosa of the nose, mouth, eye, ear, respiratory system, vagina, urethra or rectum (severally and interchangeably termed herein "target site").

By selecting a suitable active agent, or a combination of at least two active agents, the compositions are useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non-limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment, the composition is useful for the treatment of wound, ulcer and burn. This use is particularly important since the composition creates a thin, semi-occlusive layer, which coats the damaged tissue, while allowing exudates to be released from the tissue.

The composition is also suitable for administering a hormone to the skin or to a mucosal membrane or to a body cavity, in order to deliver the hormone into the tissue of the target organ, in any disorder that responds to treatment with a hormone.

In some embodiments, the target site for administration or delivery of the carriers described herein includes, without limitation, the skin, a body cavity, a mucosal surface, the nose, the mouth, the eye, the ear canal, the respiratory system, the vagina and the rectum.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

The carriers may be used as a substitute for ointment-based formulations when petrolatum is not desirable because it causes disturbance: too greasy, too occlusive, does not allow exudates to be released (like in wound & burn). It can also be used for treatment of disorders wherein the cosmetic elegance is an issue, like acne, rosacea (where the active agent requires water free environment, as specified above).

In one or more embodiments, the composition may be used for cosmetic use. For example it may be used as part of a cosmetic formulation to prevent a cosmetic disorder or to improve the skin. Alternatively it may be used with cosmetic effect for example as a cosmetic remover. It can be dispensed in small quantities as a foam targeted to a surface and applied locally with mechanical force causing the foam to break.

The invention is described with reference to the following examples. This invention is not limited to these examples and experiments. Many variations will suggest themselves and are within the full intended scope of the appended claims.

Methodology

The carriers and pharmaceutical formulations may be made in the following general way with appropriate adjustments for each formulation as will be appreciated by someone skilled in the art. Stabilizing surfactants added usually with heat, until a homogeneous mixture is obtained, the mixture is then allowed to cool. The remainder of the ingredients, if any, are then added with mixing until they have dissolved in the medium. The active agent is usually added at the end incorporated. For foam the canisters are then filled with the above waterless formula, sealed and crimped with a valve and pressurized with the propellant.

A general procedure for preparing foamable carriers is set out in WO 2004/037225, which is incorporated herein in its entirety by reference.

Oily Waterless Foam 1. a) Heat oil to about 65° C. to about 70° C. mixing with a homogenizer; b) add surfactant(s) under mixing with a homogenizer until any solids are completely liquefied; c) where applicable, make a premix of heat sensitive ingredients (active agents) with about a quarter part of oil at room temperature and set aside; d) Mix b. well and cool rapidly to about below about 35° C. by plunging the container into an ice bath while stirring; and add c) the premix of sensitive ingredients with moderate mixing at about below 30° C.; e) Cool to room temperature quickly.

2. Alternatively, cooling may be carried out slowly with stirring by simply leaving the container with the contents stirring in a room, which is at room temperate. Note that whilst cooling at stage d. is preferred to about below 30° C. before adding sensitive ingredients, such as tetracycline antibiotics, for formulations with less (or no sensitive) ingredients cooling may optionally be to about below 35° C. (or about below 40° C.).

Production Under Vacuum

Optionally, the foamable carrier may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Canisters Filling and Crimping

Each aerosol canister is filled with the pre-foam formulation ("PFF", i.e., foamable carrier) and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing

Propellant Filling

Pressurizing is carried out using a hydrocarbon gas or gas mixture. Canisters are filled and then warmed for 30 seconds in a warm bath at 50° C. and well shaken immediately thereafter.

Closure Integrity Test

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Tests

By way of non-limiting example the objectives of hardness, collapse time and freeze-thaw cycle ("FTC") stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can affect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 minute. Foams which are structurally stable on the skin for at least one minute are termed "short term stable" carriers or foams.

Density

In this procedure, the foam product is dispensed into vessels (including dishes or tubes) of a known volume and weight. Replicate measurements of the mass of foam filling the vessels are made and the density is calculated. The canister and contents are allowed to reach room temperature. Shake the canister to mix the contents and dispense and discard 5-10 mL. Then dispense foam into a preweighed tube, filling it until excess is extruded Immediately remove (level off) excess foam at both ends and weigh the filled tube on the weighing balance.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

FTC (Freeze Thaw Cycles)

Foam appearance under extreme conditions of repeated heating and cooling is evaluated by cycling through cooling, heating, (first cycle) cooling, heating (second cycle) etc., conditions, commencing with −10° C. (24 hours) followed by +40° C. (24 hours) and measuring the appearance following each cycle. The cycle is repeated for up to three times.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at one or more of 5 C, at 25 C, at, 40 C and at 50 C. At appropriate time intervals canisters are removed and the amount of active agent in the foam sample is measured.

Visual Stability Tests

Spillability

An objective in designing formulations it to formulate so the composition does not lose fluidity, and stays spillable after the incorporation of active agent. Spillability means free moving or rotating of formulation inside the glass bottle upon inversion.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

The light microscope enables observing and measuring particles from few millimeters down to one micron. Light microscope is limited by the visible light wavelength and therefore is useful to measuring size of particles above 800 nanometers and practically from 1 micron (1,000 nanometers).

Shakability

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non-shakable. This property may be of particular importance in cases where shaking is required for affecting proper dispersion of the contents.

Shakability Scoring:

| Shakability | |
| --- | --- |
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Uniformity

Intra-Canister Uniformity

1. Representative product containers are collected, sample test solutions are prepared and the content of the analyte is determined according to standard methods in the art. Variability of content is characterized as percent difference or relative standard deviation, as appropriate, according to the number of samples evaluated;

2. The results ascertain variability or uniformity within a given container in content of analytes (primarily active pharmaceutical ingredients, but also preservatives) taken from different parts of a pressurized canister drug products;

3. Two full canisters were shaken according to product instructions. About 1-3 g of Foam was dispensed from each canister and discarded. Foam sufficient for two replicate sample solution preparations was then dispensed into a glass beaker. This represents the initial sample. A middle portion is then dispensed from each canister being about half the canister contents. This middle dispensed portion may be discarded or collected for testing purposes, as necessary. Foam sufficient for two replicate sample solution preparations was then dispensed into a glass beaker. This represents the final sample. A small amount of formulation remains in the canister. The foam samples were stirred to remove gas/air bubbles. From both the initial and final foam portions from each canister 4 separate sample solutions are prepared and analyzed, 2 from the initial portion and 2 from the final portion. The percent difference is calculated as follows:

$$\frac{\text{Difference between content determined in initial \& final portions}}{\text{Mean of content of initial \& final portions}} \times 100$$

and the intra canister uniformity evaluated from the results.

Stock Carriers

Non-limiting examples of how stock solutions are made up with and without API are illustrated. Other stock solutions may be made using the same methodology by simply varying adding or omitting ingredients as would be appreciated by one of the ordinary skills in the art.

EXAMPLES

The invention is described with reference to the following examples. For the purpose of the Examples below it was sufficient to apply a vacuum only at the crimping stage although for long term stability preferably any vacuum should be applied during manufacture as well at a sufficient pressure so that any oxygen remaining in the formulation is virtually negligible. This invention is not limited to these examples and experiments. Many variations will suggest themselves and are within the full intended scope of the appended claims.

A list of the chemical constituents of the Brand names of some of the ingredients, used in some of the formulations appears in below in Table 3.

TABLE 3

INGREDIENTS

| Ingredients | brand name | category | HLB | RHLB |
|---|---|---|---|---|
| Heavy Mineral Oil | Paraffin oil liquid heavy | Solvent | | 10.5 |
| Light Mineral Oil | Pionier 2076P | Solvent | | 10.5 |
| Soybean Oil | Soybean Oil | Solvent | | 7 |
| Jojoba Oil | Jojoba Oil | Solvent | | 6 |
| Manuka Oil | Manuka Oil | Solvent | | |
| Cetearyl alcohol and cetearyl glucoside | Montanov 68 | Surfactant | | |
| C14-C22 alkyl alcohol C12-C20 alkyl glucoside | Montanov L | Surfactant | | |
| Glyceryl monostearate | Cutina GMS V PH | Surfactant | 3.8 | |
| Glyceryl monooleate | Monomuls 90-018 | Surfactant | 3.8 | |
| Glyceryl distearate | Glyceryl distearate | Surfactant | 2.4 | |
| Cetearyl alcohol | Speziol C16-C18 | Foam adjuvant | | |
| α-tocopherol | | API and oil | | |
| Minocycline HCl | Minocycline HCl | API | | |
| Betamethasone Valerate | Betamethasone Valerate | API | | |
| Terbinafine | Terbinafine | API | | |
| Metronidazole | Metronidazole | API | | |
| Calcitriol | Calcitriol | API | | |
| Naproxen | Naproxen | API | | |
| Propane/butane/isobutane (20:78:2) | A-46 | Propellant | | |
| Propane/butane/isobutane (55:18:27) | AP-70 | Propellant | | |

API = Active Pharmaceutical Ingredient

Example 1

Slow vs. Rapid Cooling Procedures on Foam Produced by Heavy Mineral Oil and Glyceryl Monostearate

| Ingredients | 012 | 013 |
|---|---|---|
| Cooling | Rapid | Slow |
| Heavy mineral oil | 96.00 | 96.00 |
| Glyceryl monostearate | 4.00 | 4.00 |
| Total | 100.00 | 100.00 |

-continued

| Ingredients | 012 | 013 |
|---|---|---|
| Propellant (AP70) | 8.00 | 8.00 |
| Results PFF | | |
| Viscosity 10 RPM | 6494.61 | 4447.05 |
| Foam | | |
| Quality | Good/Excellent | Good/Excellent |
| Color | white | white |
| Odor | No odor | No odor |
| Shakability | good | Good |
| Density | 0.185 | 0.205 |
| Hardness | 25.33 | 32.33 |

Procedure A 012-081022:
Heavy mineral oil was heated to ~60° C., followed by the addition of glyceryl monostearate until fully dissolved. The mixture was cooled rapidly to 30° C. using an ice bath and allowed to reach room temperature while stirring.

Procedure B 013-081022:
Heavy mineral oil was heated to ~60° C., followed by the addition of glycerol stearate until fully dissolved. The mixture was allowed to reach room temperature slowly while stirring.

Foam quality was similar following the two procedures and was of a high quality. Viscosity of the PFF was lower following the slow procedure.

Interestingly the color of the PFF was brighter following the fast cooling procedure.

Example 2

Rapid Cooling Comparison of Three Surfactants, One from Glycerol Fatty Acid Derivatives—and Two from Alkyl Alcohol/Alkyl Glucosides

| Ingredients | 038A | 040A | 039A |
|---|---|---|---|
| Procedure | (I) Rapid to 27-30° C. (II) RT | | |
| Heavy Mineral Oil | 96.00 | 96.00 | 96.00 |
| Glyceryl monooleate (Monomuls 90-018) | 4.00 | | |
| Montanov 68 (cetearyl alcohol and cetearyl glucosides) | | 4.00 | |
| Montanov L (C14-C22 Alkylalcohol and C12-20 Alkylglucoside) | | | 4.00 |
| Total | 100.00 | 100.00 | 100.00 |
| Propellant(propane + butane + isobutane) A70 | 8.00 | 8.00 | 8.00 |
| RESULTS PFF | | | |
| Viscosity (10 RPM) | NA | NA | NA |
| Foam | | | |
| Foam Quality | Fairly good | Fairly good | Fairly good |
| Color | white | white | white |
| Odor | No odor | No odor | No odor |
| Shakability | Good | Good | Good |

Mineral oil was heated to ~60-65° C., followed by the addition of glyceryl monoleate or cetearyl alcohol and cetearyl glucosides or C14-C22 Alkylalcohol and C12-20 Alkylglucoside, until fully dissolved. The mixture was cooled instantly to 27-30° C. using an ice bath. The mixture was cooled to room temperature.

Surprisingly, when a surfactant from the same family (glycerides of fatty acids)—Glyceryl monooleate (Monomuls) was used, the foam quality was fairly good and this surfactant was not as successful as its close relative glyceryl monostearate, which produced a high quality foam as seen in Example 1. Increasing the amount of glyceryl monooleate to 5% and using a higher pressure propellant did not improve foam quality as can be seen from Example 8.

Without being bound to any theory, perhaps the difference can be attributed to the double bond present in the monooleate fatty acid chain. It appears that glyceryl monostearate, which has a saturated straight fatty acid chain, plays an important role in the foam quality since glyceryl monostearate and mineral oil produced foam of high quality. It may be postulated that linear side chains are preferred over branched or unsaturated.

Example 3

Slow Cooling Light Mineral Oil and Propellant, with and without Glyceryl Monostearate and with and without Cetearyl Alcohol

| Ingredients | 060 | 061 | 062 |
|---|---|---|---|
| Light Mineral Oil | 100.00 | 92.00 | 95.00 |
| Glyceryl monostearate | — | 8.00 | — |
| Cetearyl alcohol | | | 5.00 |
| Total | 100.00 | 100.00 | 100.00 |
| Propellant(propane + butane + isobutane) A70 | 8.00 | 8.00 | 8.00 |
| RESULTS | | | |
| Foam Quality | Poor | Fairly Good | Fairly good |

Procedure 060: propellant was introduced to light mineral oil.

Procedure 061: light mineral oil was heated to 60-65° C. followed by the addition of glyceryl monostearate until fully dissolved. The mixture was cooled slowly and propellant was introduced.

Procedure 062: light mineral oil was mixed and heated to 60-65° C. followed by the addition of Cetearyl alcohol until fully dissolved. The mixture was cooled slowly to about 40-45° C.

Light mineral oil alone does not produce foam as shown in formulation 060. The addition of surfactant or foam adjuvant to light mineral oil only produces foams of fairly good quality. Without being bound by any theory, it may be that oils of low viscosity such as light mineral oil are less prone to foaming than oils of high viscosity such as heavy mineral oil. Other factors like the lower amount of propellant and slow cooling used may or may not be relevant.

Example 4

Rapid Cooling with Heavy Mineral Oil, Glyceryl Monostearate and Alpha Tocoperol Effect of API (Active Pharmaceutical Ingredient)

| Ingredients | 027 |
|---|---|
| Procedure | Rapid cooling to 30° C. |
| Heavy mineral oil | 96.00 |
| Glyceryl monostearate | 4.00 |
| Alpha tocoperol | 0.01 |
| Total | 100.01 |
| Propellant (AP70) | 8.00 |
| Results | |
| PFF | |
| Viscosity (cPi) | NA |
| Foam | |
| Quality | Good |
| Color | white |
| Odor | No odor |
| Shakability | good |
| Density (g/mL) | NA |
| Collapse | >180/G |

Procedure

Mineral oil was heated to ~60° C., followed by the addition of glyceryl monostearate until full dissolution. The mixture was cooled rapidly to 30-35° C. using an ice bath. The mixture was allowed to reach room temperature while stirring. Alpha tocoperol was added.

The addition of an API did not substantially alter the foam quality.

Example 5

Slow Cooling Formulations with Glyceryl Monostearate Comparing Various Hydrophobic Solvents Formulations were prepared, containing various hydrophobic solvents checked for their foaming properties. As described in the table below, formulations containing substantial amounts of heavy minearl oil and soybean oil provided good quality as shown in formulation 101 and 102, whereas formulation containing Jojoba oil produced foams of fairly good quality.

| | Formulation | | | |
|---|---|---|---|---|
| Ingredients | 101 % w/w | 102 % w/w | 113 % w/w | 114 % w/w |
| Heavy mineral oil | 96.00 | — | — | 90.00 |
| Soybean oil | — | 96.00 | — | — |
| Jojoba oil | — | — | 96.00 | — |
| Manuka oil | — | — | — | 6.00 |
| Glyceryl Monostearate | 4.00 | 4.00 | 4.00 | 4.00 |
| Total | 100.00 | 100.00 | 100.00 | 100.00 |
| Propellant A46 | 12.00 | 12.00 | 12.00 | 12.00 |

-continued

| | Formulation | | | |
|---|---|---|---|---|
| Ingredients | 101 % w/w | 102 % w/w | 113 % w/w | 114 % w/w |
| Results | | | | |
| Foam quality | Good | Good | FG | Good |
| Color | White | White | White | White |
| Odor | No odor | No odor | No odor | Characteristic odor |
| Shakability | Good | Good | Good | Good |

Manufacturing Procedure: the hydrophobic solvent was heated to 60-70° C., followed by the addition of glyceryl monostearate until complete dissolution. The mixture was allowed to reach room temperature slowly while stirring. The formulation was packaged in aerosol canisters which were crimped with a valve, pressurized with propellant and equipped with an actuator suitable for foam dispensing. The formulation was also packaged without propellant in glass vials.

Figure 1B:
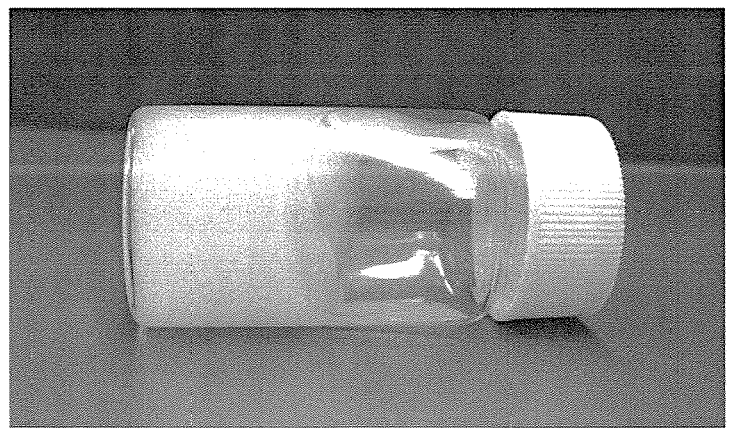

Formulation 101, observed in a glass vial before addition of propellant, was an opaque semi solid as can be seen in FIG. 1. It follows that the glyeride surfactant itself has a solidifying effect on the oil. Microscopic observation of the formulation shows the presence of glyceride crystals. However, Formulation 101 after addition of propellant, in an homogeneous opaque liquid, which demonstrates that the addition of propellant interferes with the gelling effect of the glyceride surfactant, reduces the formulation viscosity and enables flowability within pressurized containers. The observation that jojoba oil produces a foam of lower quality than the others was unexpected.

Example 6

Slow Cooling Formulations Containing a Range of Surfactant Concentrations

Formulations were prepared, containing various concentrations of glyceryl monostearate and checked for their foaming properties including bubble size.

Manufacturing Procedure: Heavy mineral oil was heated to 60-70° C., followed by the addition of glyceryl monostearate until complete dissolution. The mixture was allowed to reach room temperature while stirring. The formulation was packaged in aerosol canisters which were crimped with a valve, pressurized with propellant and equipped with an actuator suitable for foam dispensing.

As described in the table below, formulations containing up to 2% of surfactant merely generated bubbly liquids as shown in formulations 103 and 104, whereas formulations containing 4% of surfactant and more provided good quality as shown in formulation 106 and 107. Formulation 105 with 3% surfactant provided fairly good foam. Furthermore, the influence of glyceride on foam bubble size has been observed. Formulation 104 containing 2% glyceride has a very large bubble size, which is characteristic of very unstable foam. The average bubble size was in excess of a mm, which is readily visible to the eye. Formulations 106 and 112, containing respectively 4% and 10% of glycerides demonstrate a fine bubble structure with a 10 fold improvement in bubble size compared to formulation 104. Moreover increasing the surfactant to 10% did not result in a further improved bubble size. Such fine bubble structure seen in formulation 106 is highly desirable, as it combines pleasant aesthetic properties with high physical foam stability using a low amount of a nonionic surfactant. Consistent with the above observations on bubble size and quality it can be note from formulation 105 that when the level of surfactant was 3% the bubble size was about less than half that of formulation 104 with 2% surfactant but still with an average bubble size of about four times that of formulation 106 with 4% surfactant. So there is a clear relationship between the amount of surfactant, bubble size and foam quality. Thus, a concentration of about 4% glycerides seem to be optimal since it favors a) a good foam quality; b) a good flowability of the formulation within the canister; c) a fine bubble structure and d) a low amount of surfactant which reduces the risk of skin irritation.

| Formulation Ingredients | 103 % w/w | 104 % w/w | 105 % w/w | 106 % w/w | 107 % w/w | 112 % w/w |
|---|---|---|---|---|---|---|
| Heavy mineral oil | 99.00 | 98.00 | 97.00 | 96.00 | 95.00 | 90.00 |
| Glyceryl Monostearate | 1.00 | 2.00 | 3.00 | 4.00 | 5.00 | 10.00 |
| Total | 100.00 | 100.00 | 100.00 | 100.00 | 100.00 | 100.00 |
| Propellant A46 | 12.00 | 12.00 | 12.00 | 12.00 | 12.00 | 12.00 |
| Results | | | | | | |
| Foam quality | F | F | FG | Good | Good | Good |
| Color | White | White | White | White | White | White |
| Odor | No odor | No odor | No odor | No odor | No odor | No odor |
| Shakability | Good | Good | Good | Good | Good | Moderate |
| Bubble Size (micrometers) | — | 1180 | 424 | 94 | — | 121 |

Example 7

Slow Cooling Oleaginous Formulations Containing Different Active Ingredients Several active ingredients (API's) were added to oleaginous formulations based on mineral oil and glyceryl monostearate in order to assess the compatibility between the oleaginous foam vehicle and the APIs.

Manufacturing Procedure: Heavy mineral oil was heated to 60-70° C., followed by the addition of glyceryl monostearate until complete dissolution. The mixture was allowed to reach 30-40° C. and the active ingredient was added under mixing until formulation homogeneity is obtained. The mixture was allowed to reach room temperature slowly while stirring. The formulation was packaged in aerosol canisters which were crimped with a valve, pressurized with propellant and equipped with an actuator suitable for foam dispensing.

Formulation 107 containing 5% surfactant produced fairly good quality foams in presence of minocycline whereas good quality foams were obtained when the surfactant was increased to 6%. Formulations 107C to 107G, containing 5% surfactant and Betamethasone Valerate, Terbinafine, Metronidazole, Calcitriol and Naproxen gave rise to breakable foams of good quality, showing that the disclosed oleaginous foam vehicle is adaptable and suitable for use with a wide range of active ingredients. In some cases it may be required to adjust the amount of surfactant to suit the API selected, for example as shown above with minocycline.

are especially useful glycerides in oleaginous foams, as they generate good quality foams.

Two types of propellants were utilized for the formation of foam of quality, AP 70 and AP 46. The quality of the formulation can depend upon the propellant type and its concentration. In the Examples 12% of AP46, which has a lower pressure was useded to provide a foam of quality in comparison to 8% of AP70, which provides a higher pressure. So by selecting a hydrocarbon propellant with higher pressure can sometimes allow for a lower amount of propellant.

| Formulation Ingredients | 107A % w/w | 107B % w/w | 107C % w/w | 107D % w/w | 107E % w/w | 107F % w/w | 107G % w/w |
|---|---|---|---|---|---|---|---|
| Heavy mineral oil | 95.00 | 94.00 | 95.00 | 95.00 | 95.00 | 95.00 | 95.00 |
| Glyceryl Monostearate | 5.00 | 6.00 | 5.00 | 5.00 | 5.00 | 5.00 | 5.00 |
| Total | 100.00 | 100.00 | 100.00 | 100.00 | 100.00 | 100.00 | 100.00 |
| Minocycline HCl | 1.00 | 1.00 | — | — | — | — | — |
| Betamethasone Valerate | — | — | 0.12 | — | — | — | — |
| Terbinafine | — | — | — | 1.00 | — | — | — |
| Metronidazole | — | — | — | — | 1.00 | — | — |
| Calcitriol | — | — | — | — | — | 0.05 | — |
| Naproxen | — | — | — | — | — | — | 5.00 |
| Propellant A46 | 12.00 | 12.00 | 12.00 | 12.00 | 12.00 | 12.00 | 12.00 |
| Results | | | | | | | |
| Foam quality | FG | Good | Good | Good | Good | Good | Good |
| Shakability | Good | Good | Good | Good | Good | Good | Good |
| Odor | No odor | No odor | No odor | No odor | No odor | No odor | No odor |
| Presence of API crystals | Yes | Yes | No | Yes | Yes | No | Yes |

Example 8

Slow Cooling Oleaginous Formulations Comparing Different Glycerides and Combinations Thereof Formulations were prepared, containing a glyceride alone or with a combination of glycerides, such as glyceryl monostearate, glyceryl monooleate and glyceryl distearate and checked for their foaming properties.

Manufacturing Procedure: Heavy mineral oil was heated to 60-70° C., followed by the addition of surfactant until complete dissolution. The mixture was allowed to reach room temperature slowly while stirring. The formulation was packaged in aerosol canisters which were crimped with a valve, pressurized with propellant and equipped with an actuator suitable for foam dispensing.

As described in the table below, formulations 108 and 110 containing unsaturated glyceryl monooleate alone or in combination glyceryl monostearate did not give rise to quality foams but generated bubbly liquids. Combinations of glyceryl monostearate with glyceryl distearate produced fairly good quality foams as shown in formulation 111. This was unexpected since each ingredient on its own provided good quality foam and may indicate that the combination interferes with or damages the structure of the surfactant—oil chains. Formulation 109 containing 5% glyceryl distearate produced good quality foams that were stable at 36° C. Thus, it has been discovered that glyceryl monostearate and glyceryl distearate

| | Formulation | | | | |
|---|---|---|---|---|---|
| Ingredients | 107 % w/w | 108 % w/w | 109 % w/w | 110 % w/w | 111 % w/w |
| Heavy mineral oil | 95.00 | 95.00 | 95.00 | 95.00 | 95.00 |
| Glyceryl monostearate | 5.00 | — | — | 2.50 | 2.50 |
| Glyceryl monooleate | — | 5.00 | — | 2.50 | — |
| Glyceryl distearate | — | — | 5.00 | — | 2.50 |
| Total | 100.00 | 100.00 | 100.00 | 100.00 | 100.00 |
| Propellant A46 | 12.00 | 12.00 | 12.00 | 12.00 | 12.00 |
| Results | | | | | |
| Foam quality | Good | F | Good | F | FG |
| Shakability | Good | Good | Good | Good | Good |
| Odor | No odor | No odor | No odor | No odor | No odor |

Example 9

Formulation with Some Optional Components

Formulation 115 was prepared, containing oils, glyceryl monostearate and additional components such as: additional surfactants (ceteareth-20 and sorbitan stearate, PEG-100 stearate), silicone oil (cyclomethicone), thickeners (lanolin, myristyl alcohol, behenyl alcohol), emollient (PPG-15 stearyl ether) and active ingredient (calcipotriol). The formulation provided a breakable foam of good quality.

| Ingredients | Formulation 115 % w/w |
|---|---|
| Octyl dodecanol | 10.00 |
| Light mineral oil | 25.00 |
| Heavy mineral oil | 9.50 |
| Cyclomethicone | 5.00 |
| MCT oil | 30.00 |
| Ceteareth-20 | 2.00 |
| Glyceryl monostearate | 4.00 |
| Sorbitan stearate | 2.00 |
| GMS/PEG 100 stearate | 3.00 |
| Lecithin | 1.40 |
| Myristyl alcohol | 2.00 |
| Behenyl alcohol | 1.10 |
| PPG-15 Stearyl ether | 4.99011 |
| Calcipotriol | 0.00989 |
| Total | 100.00 |
| Propellant AP-70 | 8.00 |
| Results | |
| Foam quality | Good |
| Shakability | Good |
| Odor | No odor |

What is claimed is:

1. A waterless foamable pharmaceutical composition, comprising a foamable carrier, a tetracycline antibiotic, and at least one liquefied or compressed gas propellant wherein the foamable carrier comprises: about 60% to about 98% by weight a liquid oil comprising a mixture of a mineral oil and one or more liquid oils selected from the group consisting of a medium chain triglyceride oil, a liquid paraffin, a vegetable oil, an essential oil and a silicone oil; and about 2% to about 40% by weight of a first surfactant, wherein the surfactant comprises a glycerol fatty acid ester having a $C_8$-$C_{24}$ saturated hydrocarbon chain; and optionally an additive selected from the group consisting of a foam adjuvant, a polymer stabilizer, a thickener, a phospholipid and mixtures of any two or more thereof, wherein the foamable carrier has compatibility with the tetracycline antibiotic such that the tetracycline antibiotic is chemically stable for at least 72 hours at 25° C. in the presence of the foamable carrier; and wherein the foamable carrier is substantially a single phase, is in a compatible canister and wherein upon dispensing the foamable composition forms a breakable foam that is thermally stable at 36° C., yet breaks upon application of shear force.

2. The waterless foamable pharmaceutical composition of claim 1, wherein the average bubble size of the foam is less than about 200 microns.

3. The waterless foamable pharmaceutical composition of claim 1, wherein the composition further comprises an additional surfactant selected from the group consisting of a polysorbate, polyoxyethylene (20) sorbitan monostearate, polyoxyethylene (20) sorbitan monooleate, a polyoxyethylene fatty acid ester, polyoxyethylene (8) stearate, polyoxyethylene (20) stearate, polyoxyethylene (40) stearate, polyoxyethylene (100) stearate, a polyoxyethylene alkyl ether, polyoxyethylene cetyl ether, a steareth, steareth 2, steareth 21, polyoxyethylene (23) cetyl ether, polyoxyethylene (2) cetyl ether, polyoxyethylene (10) cetyl ether, a sucrose ester, a partial ester of sorbitol and its anhydrides, sorbitan monolaurate, isoceteth-20 and mono-, and di- and tri-esters of sucrose with fatty acids, and mixtures of any two or more thereof.

4. The waterless foamable pharmaceutical composition of claim 1, wherein the glycerol fatty acid ester is selected from the group consisting of glyceryl monostearate, glyceryl behenate, glyceryl palmitostearate, and mixtures of any two or more thereof.

5. The waterless foamable pharmaceutical composition of claim 1, wherein the glycerol fatty acid ester is a solid.

6. The waterless foamable pharmaceutical composition of claim 1, wherein the mineral oil is a mixture of light mineral oil and heavy mineral oil.

7. The waterless foamable pharmaceutical composition of claim 6, wherein the weight ratio of the light mineral oil to the heavy mineral oil ranges from about 1:1 to about 1:2.

8. The waterless foamable pharmaceutical composition of claim 1, further comprising an additional active agent.

9. The waterless foamable pharmaceutical composition according to claim 8, wherein the additional active agent is soluble in the liquid oil, the glycerol fatty acid ester or the carrier.

10. The waterless foamable pharmaceutical composition according to claim 8, wherein the foamable carrier including the additional active agent is a homogenous suspension.

11. The waterless foamable pharmaceutical composition of claim 8, wherein the additional active agent is selected from the group consisting of an acaricide, an active herbal extract, an age spot and keratose removing agent, an allergen, an alpha hydroxy acid, an analgesic agent, an androgen, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an anti-hyperkeratosis agent, an anti-infective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an anti-yeast agent, an astringent, a beta-hydroxy acid, benzoyl peroxide, a cardiovascular agent, a chemotherapeutic agent, a corticosteroid, an immunogenic substance, a dicarboxylic acid, a disinfectant, an estrogen, a fungicide, a hair growth regulator, a haptene, a hormone, a hydroxy acid, an immunosuppressant, an immunoregulating agent, an immunomodulator, an immunostimulant, an insecticide, an insect repellent, a keratolytic agent, a lactam, a local anesthetic agent, a lubricating agent, a masking agent, a metal, a metal oxide, a mitocide, a neuropeptide, a non-steroidal anti-inflammatory agent, an oxidizing agent, a pediculicide, a peptide, a pesticide, a progesterone, a protein, a photodynamic therapy agent, a radical scavenger, a refatting agent, a retinoid, a sedative agent, a scabicide, a self tanning agent, a skin protective agent, a skin whitening agent, a steroid, a steroid hormone, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin derivative, a wound healing agent, a wart remover and mixtures of any two or more thereof.

12. The waterless foamable pharmaceutical composition of claim 8, wherein the glycerol fatty acid ester induces the oil based formulation to gel.

13. The waterless foamable composition of claim 1, wherein the tetracycline antibiotic agent is selected from the group consisting of a minocycline, a doxycycline and mixtures of any two or more thereof.

14. The waterless foamable pharmaceutical composition of claim 8, wherein the additional active agent is selected from the group consisting of acyclovir, azelaic acid, clindamycin phosphate, pimecrolimus, diclofenac potassium, calcipotriol, calcitriol, vitamin A acetate, betamethasone 17-valerate, alpha tocopherol, imiquimod, ciclopiroxolamine, and mixtures of any two or more thereof.

15. The waterless foamable pharmaceutical composition of claim 1, wherein the composition further comprises one or more additional components selected from the group consisting of anti-perspirants, anti-static agents, buffering agents, anti-oxidants, free radical scavengers, bulking agents, chelating agents, cleansers, colorants, conditioners, deodorants, diluents, dyes, fragrances, hair conditioners, humectants, modulating agents, pearlescent aids, perfuming agents, permeation enhancers, pH-adjusting agents, occlusive agents, preservatives, protectants, skin penetration enhancers, softeners, solubilizers, sunscreens, sun blocking agents, sunless tanning agents, viscosity modifiers, and vitamins.

16. A waterless foamable pharmaceutical composition, comprising a foamable carrier, a tetracycline antibiotic, and at least one liquefied or compressed gas propellant wherein the foamable carrier comprises: about 60% to about 98% by weight of a liquid oil comprising a mixture of a mineral oil and one or more liquid oils selected from the group consisting of a medium chain triglyceride oil, a liquid paraffin, a vegetable oil, an essential oil and a silicone oil; about 2% to about 40% by weight of surfactant, wherein the surfactant comprises a glycerol fatty acid ester having a $C_8$-$C_{24}$ saturated hydrocarbon chain; and an additive selected from the group consisting of a foam adjuvant and a polymer stabilizer, wherein the foamable carrier has compatibility with the tetracycline antibiotic such that the tetracycline antibiotic is chemically stable for at least 72 hours at 25° C. in the presence of the foamable carrier; and wherein the foamable carrier is substantially a single phase in a compatible canister and wherein upon dispensing the foamable composition forms a breakable foam that is thermally stable at 36° C., yet breaks upon application of shear force.

17. The waterless foamable pharmaceutical composition of claim 16, wherein the additive is a foam adjuvant, which is selected from the group consisting of a fatty alcohol, a fatty acid and a hydroxyl fatty acid.

18. The waterless foamable pharmaceutical composition of claim 1, wherein the liquid oil is a mixture of a vegetable oil, a mineral oil, and a silicone oil.

19. The waterless foamable pharmaceutical composition of claim 1, wherein the liquid oil contains a wax.

20. The waterless foamable pharmaceutical composition of claim 16, wherein the average bubble size of the foam is less than about 200 microns.

21. The waterless foamable pharmaceutical composition of claim 16, wherein the glycerol fatty acid ester is selected from the group consisting of glyceryl monostearate, glyceryl behenate, glyceryl palmitostearate, and mixtures of any two or more thereof.

22. The waterless foamable pharmaceutical composition of claim 16, further comprising an additional active agent.

23. The waterless foamable pharmaceutical composition according to claim 22, wherein the additional active agent is soluble in the liquid oil, the glycerol fatty acid ester or the carrier.

24. The waterless foamable pharmaceutical composition according to claim 22, wherein the foamable carrier including the additional active agent is a homogenous suspension.

25. The waterless foamable pharmaceutical composition of claim 22, wherein the additional active agent is selected from the group consisting of an acaricide, an active herbal extract, an age spot and keratose removing agent, an allergen, an alpha hydroxy acid, an analgesic agent, an androgen, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an anti-hyperkeratosis agent, an anti-infective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an anti-yeast agent an astringent, a beta-hydroxy acid, benzoyl peroxide, a cardiovascular agent a chemotherapeutic agent, a corticosteroid, an immunogenic substance, a dicarboxylic acid, a disinfectant, an estrogen, a fungicide, a hair growth regulator, a haptene, a hormone, a hydroxy acid, an immunosuppressant, an immunoregulating agent, an immunomodulator, an immunostimulant, an insecticide, an insect repellent, a keratolytic agent, a lactam, a local anesthetic agent, a lubricating agent, a masking agent, a metal, a metal oxide, a mitocide, a neuropeptide, a non-steroidal anti-inflammatory agent, an oxidizing agent, a pediculicide, a peptide, a pesticide, a progesterone, a protein, a photodynamic therapy agent, a radical scavenger, a refatting agent, a retinoid, a sedative agent, a scabicide, a self tanning agent, a skin protective agent, a skin whitening agent, a steroid, a steroid hormone, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent, a wart remover and mixtures of any two or more thereof.

26. The waterless foamable pharmaceutical composition of claim 23, wherein the glycerol fatty acid ester induces the oil based formulation to gel.

27. The waterless foamable composition of claim 16, wherein the tetracycline antibiotic agent is selected from the group consisting of a minocycline, a doxycycline and mixtures of any two or more thereof.

28. The waterless foamable pharmaceutical composition of claim 16, wherein the composition further comprises one or more additional components selected from the group consisting of anti-perspirants, anti-static agents, buffering agents, anti-oxidants, free radical scavengers, bulking agents, chelating agents, cleansers, colorants, conditioners, deodorants, diluents, dyes, fragrances, hair conditioners, humectants, modulating agents, pearlescent aids, perfuming agents, permeation enhancers, pH-adjusting agents, occlusive agents, preservatives, protectants, skin penetration enhancers, softeners, solubilizers, sunscreens, sun blocking agents, sunless tanning agents, viscosity modifiers, and vitamins.

29. The waterless foamable pharmaceutical composition of claim 16, wherein the liquid oil is a mixture of a vegetable oil, a mineral oil, and a silicone oil.

30. The waterless foamable pharmaceutical composition of claim 16, wherein the liquid oil contains a wax.

31. A waterless foamable pharmaceutical composition, consisting essentially of a foamable carrier, a tetracycline antibiotic, and at least one liquefied or compressed gas propellant, wherein the foamable carrier consists essentially of: about 60% to about 98% by weight of a liquid oil, wherein said liquid oil is a mixture of a mineral oil and one or more liquid oils selected from the group consisting of a medium chain triglyceride oil, a liquid paraffin, a vegetable oil, an essential oil and a silicone oil; and about 2% to about 40% by weight of a surfactant, wherein the surfactant is a glycerol fatty acid ester having a $C_8$-$C_{24}$ saturated hydrocarbon chain; and optionally an additive selected from the group consisting of a foam adjuvant, a polymer stabilizer, a thickener, a phospholipid and mixtures of any two or more thereof, wherein the foamable carrier has compatibility with the tetracycline antibiotic such that the tetracycline antibiotic is chemically stable for at least 72 hours at 25° C. in the presence of the foamable carrier; and wherein the foamable carrier is substantially a single phase, is in a compatible canister and wherein upon dispensing the foamable composition forms a breakable foam that is thermally stable at 36° C., yet breaks upon application of shear force.

32. The waterless foamable pharmaceutical composition of claim 1, wherein the glycerol fatty acid ester is glyceryl monostearate.

33. The waterless foamable pharmaceutical composition of claim 16, wherein the glycerol fatty acid ester is glyceryl monostearate.

34. The waterless foamable pharmaceutical composition of claim 16, wherein the glycerol fatty acid ester is a solid.

\* \* \* \* \*

UNITED STATES PATENT AND TRADEMARK OFFICE
CERTIFICATE OF CORRECTION

PATENT NO. : 8,518,376 B2  
APPLICATION NO. : 13/123213  
DATED : August 27, 2013  
INVENTOR(S) : Dov Tamarkin et al.

Page 1 of 1

It is certified that error appears in the above-identified patent and that said Letters Patent is hereby corrected as shown below:

On the Title Page, item (75), Column 1, Line 2 (Inventors), delete "Moshav Gimzu (IL);" and insert -- Moshav Gimzo (IL); --, therefor.

In the Claims:

Column 41, Line 31, In Claim 1, after "weight" insert -- of --.

Column 41, Line 35, In Claim 1, after "a" delete "first".

Column 42, Line 29, In Claim 11, delete "anent," and insert -- agent, --, therefor.

Column 42, Line 46, In Claim 11, delete "mitocide," and insert -- miticide, --, therefor.

Column 42, Line 57, In Claim 11, delete "vitamin derivative," and insert -- vitamin K derivative, --, therefor.

Column 44, Line 5, In Claim 25, delete "anent," and insert -- agent, --, therefor.

Column 44, Line 22, In Claim 25, delete "mitocide," and insert -- miticide, --, therefor.

Column 44, Line 36, In Claim 26, delete "claim 23," and insert -- claim 22, --, therefor.

Signed and Sealed this  
Ninth Day of August, 2016

Michelle K. Lee  
*Director of the United States Patent and Trademark Office*